US007998471B2

(12) United States Patent
Jacobs, Jr. et al.

(10) Patent No.: US 7,998,471 B2
(45) Date of Patent: Aug. 16, 2011

(54) MYCOBACTERIA EXPRESSING HIV-1 AND MALARIA ANTIGENS

(75) Inventors: William R. Jacobs, Jr., Pelham, NY (US); Norman L. Letvin, Newton, MA (US); Mark Cayabyab, Boston, MA (US); Barton F. Haynes, Durham, NC (US); Hua-Xin Liao, Durham, NC (US); Jae-Sung Yu, Durham, NC (US); Avi-Hai Hovav, Brookline, MA (US)

(73) Assignees: Albert Einstein College of Medicine of Yeshiva University, Bronx, NY (US); Beth Israel Deaconess Medical Center, Inc., Boston, MA (US); Duke University, Durham, NC (US)

( * ) Notice: Subject to any disclaimer, the term of this patent is extended or adjusted under 35 U.S.C. 154(b) by 0 days.

(21) Appl. No.: 11/794,373

(22) PCT Filed: Jan. 11, 2006

(86) PCT No.: PCT/US2006/000790
§ 371 (c)(1),
(2), (4) Date: Jan. 25, 2008

(87) PCT Pub. No.: WO2006/076343
PCT Pub. Date: Jul. 20, 2006

(65) Prior Publication Data
US 2008/0254061 A1    Oct. 16, 2008

Related U.S. Application Data

(60) Provisional application No. 60/643,536, filed on Jan. 12, 2005.

(51) Int. Cl.
*A61K 48/00* (2006.01)
*A61K 39/02* (2006.01)
*A61K 39/04* (2006.01)

(52) U.S. Cl. ...... 424/93.2; 424/9.1; 424/9.2; 424/200.1; 424/201.1; 424/208.1; 424/234.1; 424/93.4; 424/248.1; 435/41; 435/69.1; 435/69.3; 435/71.1

(58) Field of Classification Search .................... 424/9.1, 424/9.2, 184.1, 200.1, 201.1, 208.1, 93, 234.1, 424/93.4; 248.1; 435/41, 69.1, 69.3, 71.1
See application file for complete search history.

(56) References Cited

U.S. PATENT DOCUMENTS

| 5,504,005 | A | * | 4/1996 | Bloom et al. | .................. 435/472 |
| 5,591,632 | A | * | 1/1997 | O'Donnell et al. | ......... 435/252.3 |
| 5,736,367 | A | | 4/1998 | Haun et al. | |
| 5,773,267 | A | | 6/1998 | Jacobs et al. | |
| 5,776,465 | A | | 7/1998 | O'Donnell et al. | |
| 5,830,475 | A | * | 11/1998 | Aldovini et al. | ........... 424/200.1 |
| 6,074,866 | A | | 6/2000 | Escuyer et al. | |
| 6,235,518 | B1 | | 5/2001 | Gicquel et al. | |
| 6,372,478 | B1 | | 4/2002 | Bloom et al. | |
| 6,423,545 | B1 | | 7/2002 | Pavelka, Jr. et al. | |
| 6,472,213 | B1 | | 10/2002 | Escuyer et al. | |

OTHER PUBLICATIONS

Chujoh, Y., et al. Vaccine, vol. 20, pp. 797-804, 2002.*
Zheng, C., et al. Parasitology International, vol. 51, pp. 1-7, 2002.*
Gallo. "The End or the Beginning of the Drive to an HIV-Preventive Vaccine: a View from Over 20 years." Lancet 2005, vol. 366, pp. 1894-1898.
Gilbert et al. "HIV-1 Virologic and Immunologic Progression and Initiation of Antiretroviral Therapy Among HIV-1-Infected Subjects in a Trial of the Efficacy of Recombinant glycoprotein 120 Vaccine." The Journal of Infectious Diseases 2005, vol. 192, pp. 974-983.
The Search Report for PCT Application No. PCT/US2006/000790, dated May 8, 2006.
The Written Opinion of the International Searching Authority for PCT Application No. PCT/US2006/000790, dated May 11, 2006.
The International Preliminary Report on Patentability for PCT Application No. PCT/US2006/000790, dated May 11, 2006.

* cited by examiner

*Primary Examiner* — Rodney P. Swartz
(74) *Attorney, Agent, or Firm* — Amster, Rothstein & Ebenstein LLP

(57) ABSTRACT

Provided are recombinant mycobacteria expressing an HIV-1 antigen and a malarial antigen. Also provided are *Mycobacterium smegmatis* expressing an HIV-1 antigen. Further provided are vaccines capable of inducing an immune response in a mammal against HIV-1 and the malarial pathogen. Additionally provided are methods of inducing an immune response in a mammal against HIV-1 and a malarial pathogen. Also provided are methods of inducing an immune response in a mammal against HIV-1. The methods comprise infecting the mammal with any of the above-described mycobacteria.

14 Claims, 21 Drawing Sheets

1. As a surface antigen.
2. As a secreted antigen.
3. As an intracellular expressed antigen.

MYCOBACTERIA EXPRESSING HIV-1 AND MALARIA ANTIGENS

CROSS-REFERENCE TO RELATED APPLICATION

This is a U.S. national phase of PCT Application No. PCT/US2006/000790, filed Jan. 11, 2006, which claims the benefit of U.S. Provisional Application No. 60/643,536, filed Jan. 12, 2005.

STATEMENT REGARDING FEDERALLY SPONSORED RESEARCH OR DEVELOPMENT

The invention was made with government support under Grants No. AI45705 and AI5281 awarded by the National Institutes of Health. The government has certain rights in the invention.

BACKGROUND OF THE INVENTION

Ahmad-Nejad, P., H. Hacker, M. Rutz, S. Bauer, R. M. Vabulas, and H. Wagner. 2002. Bacterial CpG-DNA and lipopolysaccharides activate Toll-like receptors at distinct cellular compartments. Eur J Immunol 32:1958-68.

Aldovini, A., and R. A. Young. 1991. Humoral and cell-mediated immune responses to live recombinant BCG-HIV vaccines. Nature 351:479-82.

Andersson, G. E., and P. M. Sharp. 1996. Codon usage in the *Mycobacterium tuberculosis* complex. Microbiology 142:915-25.

Appay, V., D. F. Nixon, S. M. Donahoe, G. M. Gillespie, T. Dong, A. King, G. S. Ogg, H. M. Spiegel, C. Conlon, C. A. Spina, D. V. Havlir, D. D. Richman, A. Waters, P. Easterbrook, A. J. McMichael, and S. L. Rowland-Jones. 2000. HIV-specific CD8(+) T cells produce antiviral cytokines but are impaired in cytolytic function. J Exp Med 192:63-75.

Bange, F. C., F. M. Collins, and W. R. Jacobs, Jr. 1999. Survival of mice infected with *Mycobacterium smegmatis* containing large DNA fragments from *Mycobacterium tuberculosis*. Tuber Lung Dis 79:171-80.

Barouch, D. H., P. F. McKay, S. M. Sumida, S. Santra, S. S. Jackson, D. A. Gorgone, M. A. Lifton, B. K. Chakrabarti, L. Xu, G. J. Nabel, and N. L. Letvin. 2003. Plasmid chemokines and colony-stimulating factors enhance the immunogenicity of DNA priming-viral vector boosting human immunodeficiency virus type 1 vaccines. J Virol 77:8729-35.

Barouch, D. H., M. G. Pau, J. H. Custers, W. Koudstaal, S. Kostense, M. J. Havenga, D. M. Truitt, S. M. Sumida, M. G. Kishko, J. C. Arthur, B. Korioth-Schmitz, M. H. Newberg, D. A. Gorgone, M. A. Lifton, D. L. Panicali, G. J. Nabel, N. L. Letvin, and J. Goudsmit. 2004. Immunogenicity of recombinant adenovirus serotype 35 vaccine in the presence of pre-existing anti-Ad5 immunity. J Immunol 172:6290-7.

Beltan, E., L. Horgen, and N. Rastogi. 2000. Secretion of cytokines by human macrophages upon infection by pathogenic and non-pathogenic mycobacteria. Microb Pathog 28:313-8.

Calarota, S., G. Bratt, S, Nordlund, J. Hinkula, A. C. Leandersson, E. Sandstrom, and B. Wahren. 1998. Cellular cytotoxic response induced by DNA vaccination in HIV-1-infected patients. Lancet 351:1320-5.

Cheadle, E. J., D. O'Donnell, P. J. Selby, and A. M. Jackson. 2005. Closely related mycobacterial strains demonstrate contrasting levels of efficacy as antitumor vaccines and are processed for major histocompatibility complex class I presentation by multiple routes in dendritic cells. Infect Immun 73:784-94.

Connell, N. D., E. Medina-Acosta, W. R. McMaster, B. R. Bloom, and D. G. Russell. 1993. Effective immunization against cutaneous leishmaniasis with recombinant bacille Calmette-Guerin expressing the *Leishmania* surface proteinase gp63. Proc Natl Acad Sci USA 90:11473-7.

Converse, S. E., and J. S. Cox. 2005. A protein secretion pathway critical for *Mycobacterium tuberculosis* virulence is conserved and functional in *Mycobacterium smegmatis*. *J Bacteriol* 187:1238-45.

de Mendonca-Lima, L., M. Picardeau, C. Raynaud, J. Rauzier, Y. O. de la Salmoniere, L. Barker, F. Bigi, A. Cataldi, B. Gicquel, and J. M. Reyrat. 2001. Erp, an extracellular protein family specific to mycobacteria. Microbiology 147:2315-20.

de Miranda, A. B., F. Alvarez-Valin, K. Jabbari, W. M. Degrave, and G. Bernardi. 2000. Gene expression, amino acid conservation, and hydrophobicity are the main factors shaping codon preferences in *Mycobacterium tuberculosis* and *Mycobacterium leprae*. J Mol Evol 50:45-55.

Fennelly, G. J., J. L. Flynn, V. ter Meulen, U. G. Liebert, and B. R. Bloom. 1995. Recombinant bacille Calmette-Guerin priming against measles. J Infect Dis 172:698-705.

Fuller, M. J., and A. J. Zajac. 2003. Ablation of CD8 and CD4 T cell responses by high viral loads. J Immunol 170:477-86.

Gheorghiu, M., M. R. Lagranderie, B. M. Gicquel, and C. D. Leclerc. 1994. *Mycobacterium bovis* BCG priming induces a strong potentiation of the antibody response induced by recombinant BCG expressing a foreign antigen. Infect Immun 62:4287-95.

Grode, L., M. Kursar, J. Fensterle, S. H. Kaufmann, and J. Hess. 2002. Cell-mediated immunity induced by recombinant *Mycobacterium bovis* Bacille Calmette-Guerin strains against an intracellular bacterial pathogen: importance of antigen secretion or membrane-targeted antigen display as lipoprotein for vaccine efficacy. J Immunol 168: 1869-76.

Hetzel, C., R. Janssen, S. J. Ely, N. M. Kristensen, K. Bunting, J. B. Cooper, J. R. Lamb, D. B. Young, and J. E. Thole. 1998. An epitope delivery system for use with recombinant mycobacteria. Infect Immun 66:3643-8.

Honda, M., K. Matsuo, T. Nakasone, Y. Okamoto, H. Yoshizaki, K. Kitamura, W. Sugiura, K. Watanabe, Y. Fukushima, S. Haga, Y. Katsura, H. Tasaka, K. Komuro, T. Yamada, T. Asano, A. Yamazaki, and S. Yamazaki. 1995. Protective immune responses induced by secretion of a chimeric soluble protein from a recombinant *Mycobacterium bovis* bacillus Calmette-Guerin vector candidate vaccine for human immunodeficiency virus type 1 in small animals. Proc Natl Acad Sci USA 92:10693-7.

Huebner, R. E. 1996. BCG vaccination in the control of tuberculosis. Curr Top Microbiol Immunol 215:263-82.

Huster, K. M., V. Busch, M. Schiemann, K. Linkemann, K. M. Kerksiek, H. Wagner, and D. H. Busch. 2004. Selective expression of IL-7 receptor on memory T cells identifies early CD40L-dependent generation of distinct CD8+ memory T cell subsets. Proc Natl Acad Sci USA 101:5610-5.

Kaech, S. M., and R. Ahmed. 2001. Memory CD8+ T cell differentiation: initial antigen encounter triggers a developmental program in naive cells. Nat Immunol 2:415-22.

Kamath, A. B., J. Woodworth, X. Xiong, C. Taylor, Y. Weng, and S. M. Behar. 2004. Cytolytic CD8+ T cells recognizing CFP10 are recruited to the lung after *Mycobacterium tuberculosis* infection. J Exp Med 200:1479-89.

Kaufmann, S. H., and U. E. Schaible. 2005. Antigen presentation and recognition in bacterial infections. Curr Opin Immunol 17:79-87.

Kuehnel, M. P., R. Goethe, A. Habermann, E. Mueller, M. Rohde, G. Griffiths, and P. Valentin-Weigand. 2001. Characterization of the intracellular survival of *Mycobacterium avium* ssp. paratuberculosis: phagosomal pH and fusogenicity in J774 macrophages compared with other mycobacteria. Cell Microbiol 3:551-66.

Kulkarni, H. R., and S. P. Zodpey. 1999. Differential protective effect of bacillus Calmette-Guerin vaccine against multibacillary and paucibacillary leprosy in Nagpur, India. Public Health 113:311-3.

Lagranderie, M., A. M. Balazuc, B. Gicquel, and M. Gheorghiu. 1997. Oral immunization with recombinant *Mycobacterium bovis* BCG simian immunodeficiency virus nef induces local and systemic cytotoxic T-lymphocyte responses in mice. J Virol 71:2303-9.

Langermann, S., S. R. Palaszynski, J. E. Burlein, S. Koenig, M. S. Hanson, D. E. Briles, and C. K. Stover. 1994. Protective humoral response against pneumococcal infection in mice elicited by recombinant bacille Calmette-Guerin vaccines expressing pneumococcal surface protein A. J Exp Med 180:2277-86.

Lee, M. H., L. Pascopella, W. R. Jacobs, Jr., and G. F. Hatfull. 1991. Site-specific integration of mycobacteriophage L5: integration-proficient vectors for *Mycobacterium smegmatis, Mycobacterium tuberculosis*, and bacille Calmette-Guerin. Proc Natl Acad Sci USA 88:3111-5.

Letvin, N. L. 2002. Strategies for an HIV vaccine. J Clin Invest 110:15-20.

Luo, Y., X. Chen, A. Szilvasi, and M. A. O'Donnell. 2000. Co-expression of interleukin-2 and green fluorescent protein reporter in mycobacteria: in vivo application for monitoring antimycobacterial immunity. Mol Immunol 37:527-36.

MacGregor, R. R., J. D. Boyer, K. E. Ugen, K. E. Lacy, S. J. Gluckman, M. L. Bagarazzi, M. A. Chattergoon, Y. Baine, T. J. Higgins, R. B. Ciccarelli, L. R. Coney, R. S. Ginsberg, and D. B. Weiner. 1998. First human trial of a DNA-based vaccine for treatment of human immunodeficiency virus type 1 infection: safety and host response. J Infect Dis 178:92-100.

Matsumoto, S., H. Yukitake, H. Kanbara, and T. Yamada. 1998. Recombinant *Mycobacterium bovis* bacillus Calmette-Guerin secreting merozoite surface protein 1 (MSP1) induces protection against rodent malaria parasite infection depending on MSP1-stimulated interferon gamma and parasite-specific antibodies. J Exp Med 188:845-54.

McKay, P. F., J. E. Schmitz, D. H. Barouch, M. J. Kuroda, M. A. Lifton, C. E. Nickerson, D. A. Gorgone, and N. L. Letvin. 2002. Vaccine protection against functional CTL abnormalities in simian human immunodeficiency virus-infected rhesus monkeys. J Immunol 168:332-7.

Mederle, I., I. Bourguin, D. Ensergueix, E. Badell, J. Moniz-Peireira, B. Gicquel, and N. Winter. 2002. Plasmidic versus insertional cloning of heterologous genes in *Mycobacterium bovis* BCG: impact on in vivo antigen persistence and immune responses. Infect Immun 70:303-14.

Molnar-Kimber, K. L., D. H. Sterman, M. Chang, E. H. Kang, M. ElBash, M. Lanuti, A. Elshami, K. Gelfand, J. M. Wilson, L. R. Kaiser, and S. M. Albelda. 1998. Impact of preexisting and induced humoral and cellular immune responses in an adenovirus-based gene therapy phase I clinical trial for localized mesothelioma. Hum Gene Ther 9:2121-33.

Nascimento, I. P., W. O. Dias, R. P. Mazzantini, E. N. Miyaji, M. Gamberini, W. Quintilio, V. C. Gebara, D. F. Cardoso, P. L. Ho, I. Raw, N. Winter, B. Gicquel, R. Rappuoli, and L. C. Leite. 2000. Recombinant *Mycobacterium bovis* BCG expressing pertussis toxin subunit S1 induces protection against an intracerebral challenge with live *Bordetella pertussis* in mice. Infect Immun 68:4877-83.

Newton, J. A., Jr., P. J. Weiss, W. A. Bowler, and E. C. Oldfield, 3rd. 1993. Soft-tissue infection due to *Mycobacterium smegmatis*: report of two cases. Clin Infect Dis 16:531-3.

Neyrolles, O., K. Gould, M. P. Gares, S. Brett, R. Janssen, P. O'Gaora, J. L. Herrmann, M. C. Prevost, E. Perret, J. E. Thole, and D. Young. 2001. Lipoprotein access to MHC class I presentation during infection of murine macrophages with live mycobacteria. J Immunol 166:447-57.

Noss, E. H., R. K. Pai, T. J. Sellati, J. D. Radolf, J. Belisle, D. T. Golenbock, W. H. Boom, and C. V. Harding. 2001. Toll-like receptor 2-dependent inhibition of macrophage class II MHC expression and antigen processing by 19-kDa lipoprotein of *Mycobacterium tuberculosis*. J Immunol 167:910-8.

Ozinsky, A., D. M. Underhill, J. D. Fontenot, A. M. Hajjar, K. D. Smith, C. B. Wilson, L. Schroeder, and A. Aderem. 2000. The repertoire for pattern recognition of pathogens by the innate immune system is defined by cooperation between toll-like receptors. Proc Natl Acad Sci USA 97:13766-71.

Pai, R. K., M. E. Pennini, A. A. Tobian, D. H. Canaday, W. H. Boom, and C. V. Harding. 2004. Prolonged toll-like receptor signaling by *Mycobacterium tuberculosis* and its 19-kilodalton lipoprotein inhibits gamma interferon-induced regulation of selected genes in macrophages. Infect Immun 72:6603-14.

Pan, A., C. Dutta, and J. Das. 1998. Codon usage in highly expressed genes of *Haemophillus influenzae* and *Mycobacterium tuberculosis*: translational selection versus mutational bias. Gene 215:405-13.

Panina-Bordignon P, Tan A, Termijtelen A, Demotz S, Corradin G, Lanzavecchia A. 1989. Universally immunogenic T cell epitopes: promiscuous binding to human MHC class II and promiscuous recognition by T cells. Eur J Immunol 19:2237-42.

Pierre-Audigier, C., E. Jouanguy, S. Lamhamedi, F. Altare, J. Rauzier, V. Vincent, D. Canioni, J. F. Emile, A. Fischer, S. Blanche, J. L. Gaillard, and J. L. Casanova. 1997. Fatal disseminated *Mycobacterium smegmatis* infection in a child with inherited interferon gamma receptor deficiency. Clin Infect Dis 24:982-4.

Seaman, M. S., F. W. Peyerl, S. S. Jackson, M. A. Lifton, D. A. Gorgone, J. E. Schmitz, and N. L. Letvin. 2004. Subsets of memory cytotoxic T lymphocytes elicited by vaccination influence the efficiency of secondary expansion in vivo. J Virol 78:206-15.

Snapper, S. B., L. Lugosi, A. Jekkel, R. E. Melton, T. Kieser, B. R. Bloom, and W. R. Jacobs, Jr. 1988. Lysogeny and transformation in mycobacteria: stable expression of foreign genes. Proc Natl Acad Sci USA 85:6987-91.

Snapper, S. B., R. E. Melton, S. Mustafa, T. Kieser, and W. R. Jacobs, Jr. 1990. Isolation and characterization of efficient plasmid transformation mutants of *Mycobacterium smegmatis*. Mol Microbiol 4:1911-9.

Staats, H. F., C. P. Bradney, W. M. Gwinn, S. S. Jackson, G. D. Sempowski, H. X. Liao, N. L. Letvin, and B. F. Haynes.

2001. Cytokine requirements for induction of systemic and mucosal CTL after nasal immunization. J Immunol 167: 5386-94.

Stover, C. K., G. P. Bansal, M. S. Hanson, J. E. Burlein, S. R. Palaszynski, J. F. Young, S. Koenig, D. B. Young, A. Sadziene, and A. G. Barbour. 1993. Protective immunity elicited by recombinant bacille Calmette-Guerin (BCG) expressing outer surface protein A (OspA) lipoprotein: a candidate Lyme disease vaccine. J Exp Med 178:197-209.

Stover, C. K., V. F. de la Cruz, T. R. Fuerst, J. E. Burlein, L. A. Benson, L. T. Bennett, G. P. Bansal, J. F. Young, M. H. Lee, G. F. Hatfull, and et al. 1991. New use of BCG for recombinant vaccines. Nature 351:456-60.

Takahashi, H., Y. Nakagawa, C. D. Pendleton, R. A. Houghten, K. Yokomuro, R. N. Germain, and J. A. Berzofsky. 1992. Induction of broadly cross-reactive cytotoxic T cells recognizing an HIV-1 envelope determinant. Science 255:333-6.

Tobian, A. A., N. S. Potter, L. Ramachandra, R. K. Pai, M. Convery, W. H. Boom, and C. V. Harding. 2003. Alternate class I MHC antigen processing is inhibited by Toll-like receptor signaling pathogen-associated molecular patterns: *Mycobacterium tuberculosis* 19-kDa lipoprotein, CpG DNA, and lipopolysaccharide. J Immunol 171:1413-22.

Underhill, D. M., A. Ozinsky, A. M. Hajjar, A. Stevens, C. B. Wilson, M. Bassetti, and A. Aderem. 1999. The Toll-like receptor 2 is recruited to macrophage phagosomes and discriminates between pathogens. Nature 401:811-5.

Via, L. E., D. Deretic, R. J. Ulmer, N. S. Hibler, L. A. Huber, and V. Deretic. 1997. Arrest of mycobacterial phagosome maturation is caused by a block in vesicle fusion between stages controlled by rab5 and rab7. J Biol Chem 272: 13326-31.

Via, L. E., R. A. Fratti, M. McFalone, E. Pagan-Ramos, D. Deretic, and V. Deretic. 1998. Effects of cytokines on mycobacterial phagosome maturation. J Cell Sci 111 (Pt 7): 897-905.

Wang, R., D. L. Doolan, T. P. Le, R. C. Hedstrom, K. M. Coonan, Y. Charoenvit, T. R. Jones, P. Hobart, M. Margalith, J. Ng, W. R. Weiss, M. Sedegah, C. de Taisne, J. A. Norman, and S. L. Hoffman. 1998. Induction of antigen-specific cytotoxic T lymphocytes in humans by a malaria DNA vaccine. Science 282:476-80.

Wei, J., J. L. Dahl, J. W. Moulder, E. A. Roberts, P. O'Gaora, D. B. Young, and R. L. Friedman. 2000. Identification of a *Mycobacterium tuberculosis* gene that enhances mycobacterial survival in macrophages. J Bacteriol 182:377-84.

Weiss, B. G., and S. Schlesinger. 1991. Recombination between Sindbis virus RNAs. J Virol 65:4017-25.

Wherry, E. J., and R. Ahmed. 2004. Memory CD8 T-cell differentiation during viral infection. J Virol 78:5535-45.

Wherry, E. J., J. N. Blattman, K. Murali-Krishna, R. van der Most, and R. Ahmed. 2003. Viral persistence alters CD8 T-cell immunodominance and tissue distribution and results in distinct stages of functional impairment. J Virol 77:4911-27.

Wherry, E. J., V. Teichgraber, T. C. Becker, D. Masopust, S. M. Kaech, R. Antia, U. H. von Andrian, and R. Ahmed. 2003. Lineage relationship and protective immunity of memory CD8 T cell subsets. Nat Immunol 4:225-34.

Wyatt, R., P. D. Kwong, E. Desjardins, R. W. Sweet, J. Robinson, W. A. Hendrickson, and J. G. Sodroski. 1998. The antigenic structure of the HIV gp120 envelope glycoprotein. Nature 393:705-11.

Yadav, M., S. K. Roach, and J. S. Schorey. 2004. Increased mitogen-activated protein kinase activity and TNF-alpha production associated with *Mycobacterium smegmatis*-but not *Mycobacterium avium*-infected macrophages requires prolonged stimulation of the calmodulin/calmodulin kinase and cyclic AMP/protein kinase A pathways. J Immunol 172:5588-97.

Yasutomi, Y., S. Koenig, S. S. Haun, C. K. Stover, R. K. Jackson, P. Conard, A. J. Conley, E. A. Emini, T. R. Fuerst, and N. L. Letvin. 1993. Immunization with recombinant BCG-SIV elicits SIV-specific cytotoxic T lymphocytes in rhesus monkeys. J Immunol 150:3101-7.

Young, D. B., and T. R. Garbe. 1991. Lipoprotein antigens of *Mycobacterium tuberculosis*. Res Microbiol 142:55-65.

Young, S. L., M. Murphy, X. W. Zhu, P. Harnden, M. A. O'Donnell, K. James, P. M. Patel, P. J. Selby, and A. M. Jackson. 2004. Cytokine-modified *Mycobacterium smegmatis* as a novel anticancer immunotherapy. Int J Cancer 112:653-60.

Zajac, A. J., J. N. Blattman, K. Murali-Krishna, D. J. Sourdive, M. Suresh, J. D. Altman, and R. Ahmed. 1998. Viral immune evasion due to persistence of activated T cells without effector function. J Exp Med 188:2205-13.

There remains an urgent need for an effective malaria vaccine. Based on previous studies demonstrating that immunization with Msp-1 protein can protect Aotus monkeys from severe forms of malaria, the demonstration that Msp-1 can be highly expressed in BCG and elicit antibody bodes well for a recombinant BCG vaccine to minimally prime for an effective malarial response.

There is also an urgent need for an HIV vaccine. Recombinant attenuated non-pathogenic mycobacteria expressing HIV immunogens are attractive vaccine candidates because of the proven safety and immunogenicity of *Mycobacterium bovis* BCG in humans as a vaccine against tuberculosis.

An effective HIV/AIDS vaccine will likely need to elicit virus-specific neutralizing antibodies and cytotoxic T lymphocyte (CTL) responses. Although an immunogen that induces antibodies that neutralize a diversity of primary HIV-1 isolates has not yet been defined, a number of strategies are being developed for generating HIV-1-specific CTL (Letvin, 2002). However, there are problems associated with each of these approaches for eliciting CTL that will likely limit their ultimate effectiveness. Plasmid DNA has not proven nearly as immunogenic in humans as it has in laboratory animals (Calarota et al., 1998; MacGregor et al., 1998; Wang et al., 1998). The immunogenicity of replication-defective adenovirus serotype 5 is limited in human populations by pre-existing serotype-specific anti-adenovirus antibodies (Molnar-Kimber et al., 1998). Pox-vectored vaccines only elicit very short-lived immunity in humans (Andrew McMichael, personal communication) and production problems have slowed the development of alphavirus-based vaccine vectors (Weiss and Schlesinger et al., 1991). Better vector systems will therefore be needed to induce anti-HIV-1 cellular immunity and prime for broadly neutralizing antibody responses.

Mycobacteria have features that make them attractive as potential HIV-1 vaccine vectors. They can be readily engineered to stably express transgenes and can elicit long-lasting cellular and mucosal immune responses (Lagranderie et al., 1997; Mederle et al., 2002). Most importantly, they have been used successfully as vaccines. The attenuated, non-pathogenic *Mycobacterium bovis* BCG is widely used as a vaccine for tuberculosis (TB) and leprosy (Huebner, 1996; Kulkarni and Zodpey, 1999). Recombinant BCG (rBCG) vaccine constructs have shown immunogenicity and protection in murine models against various infectious agents, including *Borrelia burgdorferi, Streptococcus pneumoniae, Bordetella pertus-* sis, rodent malaria, *leishmania*, and measles virus (Connell et al., 1993; Fennelly et al., 1995; Langermann et al., 1994; Matsumoto et al., 1998; Nascimento et al., 2000; Stover et al., 1993). In murine and monkey studies, we and others have shown that rBCG-elicited antibody and cell-mediated responses against HIV-1 and SIV antigens (Almad-Nejad et al., 2002; Honda et al., 1995; Stover et al., 1991; Yasutomi et al., 1993).

*Mycobacterium smegmatis* has a number of properties that may make it an effective vaccine vector. Some *M. smegmatis* strains are non-pathogenic and commensal in humans (Bange et al., 1999; Newton et al., 1993; Pierre-Audigier et al., 1997). Unlike other mycobacterial species such as BCG that survive in host cells for months by inhibiting phagosome maturation, *M. smegmatis* is rapidly destroyed by phagolysosomal proteases in the phagosomes of infected cells (Kuchnel et al., 2001; Luo et al., 2000; Via et al., 1997; 1998). Nevertheless, *M. smegmatis* can induce cytokine production by macrophages better than pathogenic mycobacterial species (Beltan et al., 2000; Yadev et al., 2004), and can activate and induce the maturation of dendritic cells better than BCG by upregulation of MHC I and costimulatory molecules (Cheadle et al., 2005). *M. smegmatis* can also access the MHC class I pathway for presentation of mycobacterial antigens more efficiently than BCG (Neyrolles et al., 2001). The present studies were initiated to assess the ability of recombinant *M. smegmatis* to elicit HIV-1 envelope-specific CD8+ T cell responses.

Since malaria & HIV coexist in developing and underdeveloped countries, there is a need for inexpensive vaccines for either pathogen. There is also a need for more effective malaria and HIV vaccines. The present invention addresses those needs.

SUMMARY OF THE INVENTION

The present invention is directed to recombinant mycobacteria expressing an HIV-1 antigen and a malarial antigen.

Additionally, the invention is directed to vaccines comprising any of the above-identified mycobacteria, where the mycobacteria are capable of inducing an immune response in a mammal against HIV-1 and the malarial pathogen.

The invention is further directed to methods of inducing an immune response in a mammal against HIV-1 and a malarial pathogen, the methods comprising infecting the mammal with any of the above-described mycobacteria.

The invention is also directed to *Mycobacterium smegmatis* expressing an HIV-1 antigen.

The invention is additionally directed to methods of inducing an immune response in a mammal against HIV-1. The methods comprise infecting the mammal with any of the above-described mycobacteria.

DETAILED DESCRIPTION OF THE INVENTION

Figure 1:
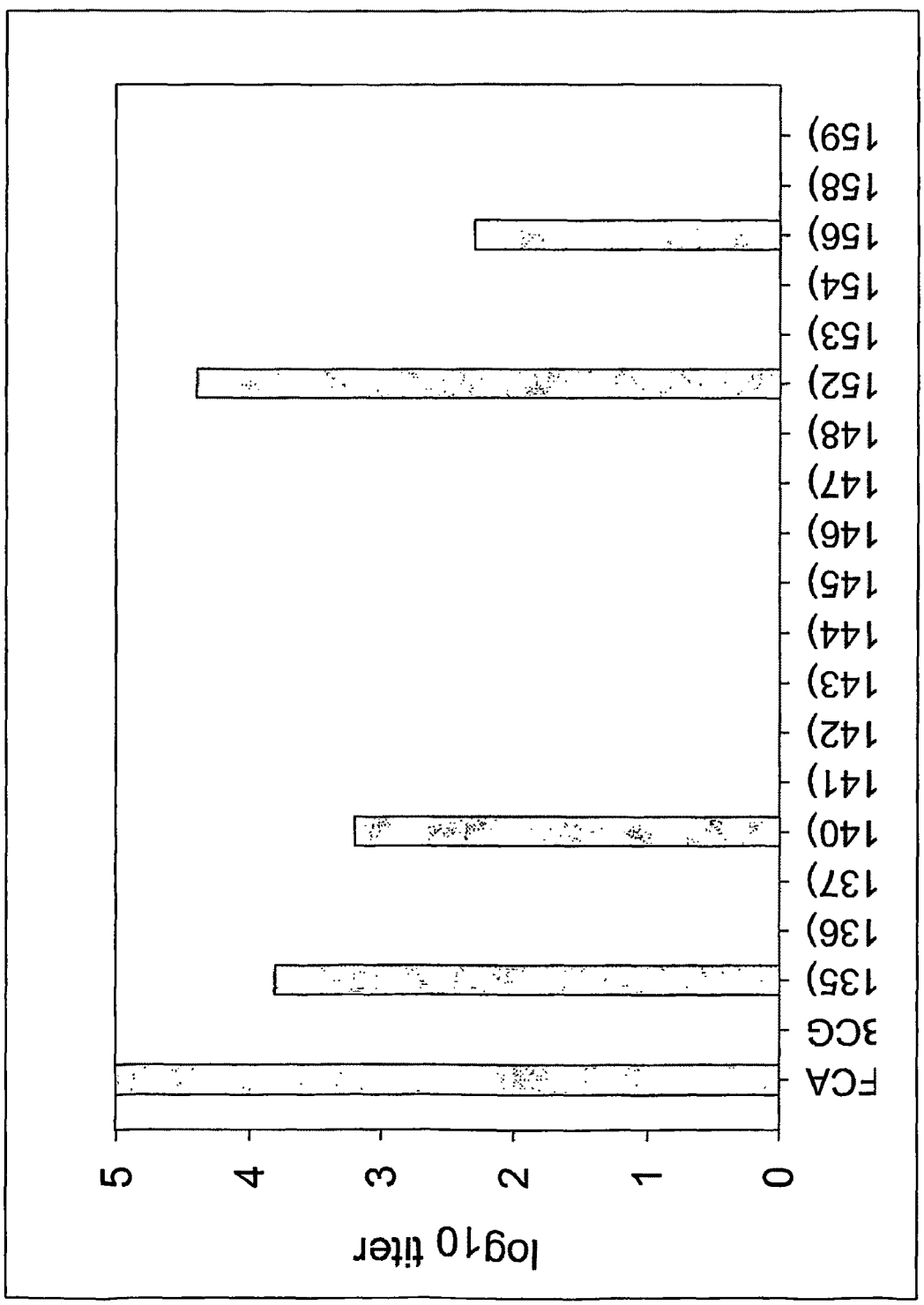
FIG. 1 is a graph showing the antibody response in Balb/c mice immunized with rBCG expressing PfMSP1-19.

The invention is directed to recombinant mycobacteria expressing an HIV-1 antigen and a malarial antigen. Since these mycobacteria are usually used in vivo, it is preferred that the mycobacteria is avirulent or rendered so, e.g., by selecting for avirulent strains or by engineering the mycobacteria to have a mutation or mutations that can fulfill that purpose. Many such mutations are known in the art, for example mutations that render the mycobacterium auxotrophic, e.g., a pan mutation or a Lys mutation, or mutations eliminating pathogenicity genes such as an RD1 deletion, as is known in the art. It is also preferred that the mycobacterium utilized for this invention can colonize the host, in order for the mycobacterium to provide a long term antigenic stimulus to the host, thus establishing a strong immune response. Non-limiting examples of useful mycobacteria are *Mycobacterium smegmatis, Mycobacterium bovis*-BCG, *Mycobacterium avium, Mycobacterium phlei, Mycobacterium fortuitum, Mycobacterium lufu, Mycobacterium paratuberculosis, Mycobacterium habana, Mycobacterium microti, Mycobacterium scrofulaceum, Mycobacterium intercellulare, Mycobacterium tuberculosis*, and any genetic variant thereof. Preferably, the mycobacterium is a *Mycobacterium smegmatis*, a *Mycobacterium bovis*-BCG, or an attenuated *Mycobacterium tuberculosis*, since those strains have been extensively studied and established to be avirulent, but able to establish a long term colonization of the host. A particularly preferred strain is *Mycobacterium smegmatis* MC$^2$155 or a derivative thereof.

Any HIV-1 antigen that can establish an immune response in the host is useful for the present invention. Examples include gp120 env, gp140 env, gp160 env, gag, pol, vif, vpr, vpu, tat, rev and nef. A preferred HIV-1 antigen is gp120 env.

Similarly, the invention is not limited to any particular malarial antigen. Preferably, the antigen is sufficiently immunogenic to establish a useful anti-malarial immune response. The antigen can be from any malarial parasite, including *Plasmodium falciparum, P. yoelii*, and *P. knowlesi* Examples of useful malarial antigens include the merozoite surface protein-1 (MSP-1) protein from *Plasmodium falciparum*, the blood stage antigen AMA-1, and the circumsporozoite antigen CSP-1. Particularly preferred is an MSP antigen. See Example 1.

Preferably, the mycobacterium is *M. smegmatis*, the viral antigen is HIV-1 gp120 or HIV-1 gp140 (env antigens), and the malarial antigen is MSP-1, since the examples (below) show that this combination establishes a strong immune response. More preferably, the malarial antigen is the MSP-1 antigen PfMSP1-19, which is the C-terminal fragment of MSP-1. Most preferably, the PfMSP1-19 antigen further comprises a portion of the PfMSP1.42 fragment that comprises most of the MSP1.33 fragment. See Example 3.

As shown in Example 1, the GC content of the gene encoding an expressed recombinant protein can affect the expression level of the protein in mycobacteria, since mycobacteria prefer genes with a high GC content. Since many malarial antigens, in particular the MSP-1 antigen, has a high AT content, engineering the gene encoding the malarial antigen to have increased GC content is effective at increasing expression of the antigen from the mycobacteria, and also increases the ability of the mycobacteria to elicit an immune response to the malaria antigen. Thus, preferably the malarial antigen is expressed from a gene that has been engineered to have an increased GC content.

It is sometimes desirable that the mycobacterium further comprises a reporter gene that is expressed when the mycobacterium infects a mammalian host, such that expression of recombinant genes from the mycobacterium can be monitored, quantified and/or localized. These embodiments are not narrowly limited to any particular reporter gene, and the skilled artisan could determine a reporter gene for any particular purpose. In some preferred embodiments, the reporter gene is a fluorescent protein or a detectable antigen.

The mycobacteria of the present invention can also utilize any promoter to drive the expression of the HIV-1 and malarial antigens. Preferred promoters are the mycobacterial promoters hsp60, mtrA, 18 kD, α-Ag, and aceA, since those promoters are known to provide sufficient expression to induce an immune response to the antigen in the host. Most preferably, the mycobacterial promoter for the HIV-1 antigen and the malarial antigen is α-Ag.

As shown in Example 1, it is also preferred if the HIV-1 antigen and the malarial antigen is expressed from genes further encoding a signal sequence that facilitates expression of the viral protein in the mycobacterial membrane. Most preferably, this signal sequence is the 19-kDa signal sequence.

Most preferably, the mycobacterium of these aspects of the invention is *M. smegmatis* MC$^2$155 or a derivative thereof; the HIV-1 antigen is gp120 env; the malarial antigen is MSP-1; the HIV-1 antigen and the malarial antigen is expressed from genes further encoding the 19-kDa signal sequence; and the mycobacterial promoter for the HIV-1 antigen and the malarial antigen is α-Ag.

The present invention is also directed to *Mycobacterium smegmatis* expressing an HIV-1 antigen. Preferably, the *M. smegmatis* is *M. smegmatis* MC$^2$155 or a derivative thereof. The HIV antigen of these *M. smegmatis* is preferably gp120 env, gp140 env, gp160 env, gag, pol, vif, vpr, vpu, tat, rev or nef; most preferably gp120 env. It is also preferred if the HIV-1 antigen is expressed from a gene further encoding the 19-kDa signal sequence, and a mycobacterial promoter for the HIV-1 antigen is α-Ag.

Most preferably, the *Mycobacterium smegmatis* is *M. smegmatis* MC$^2$155 or a derivative thereof; the HIV-1 antigen is gp120 env; the HIV-1 antigen is expressed from a gene further encoding the 19-kDa signal sequence; and the mycobacterial promoter for the HIV-1 antigen is α-Ag.

The invention is also directed to a vaccine comprising a recombinant mycobacterium expressing an HIV-1 and a malarial pathogen as described above, where the mycobacterium is capable of inducing an immune response in a mammal against HIV-1 and the malarial pathogen. Preferably, the mammal is a human.

The present invention is additionally directed to methods of inducing an immune response in a mammal against HIV-1 and a malarial pathogen. The methods comprise infecting the mammal with one of the above-described mycobacteria that expresses an HIV-1 and a malarial pathogen. Several different inoculation methods are known for infecting the mammal sufficiently to establish a long-term colonization of the mammalian host. The skilled artisan can determine without undue experimentation the most useful method of for any particular purpose.

In preferred embodiments of these methods, the mammal is a human.

The invention is further directed to methods of inducing an immune response in a mammal against HIV-1. The methods comprise infecting the mammal with any of the above-described mycobacteria.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1

Optimizing *Mycobacterium bovis* BCG Malaria Vaccines

Recombinant *Mycobacterium bovis* BCG constructs were created to optimize malarial antigen expression that elicits priming or protective immune responses to malarial antigens. BCG has the potential to deliver foreign antigens to children at birth in a developing world setting. Moreover, based on its persistence and immunogenicity, it has the potential to elicit long-lasting immune responses.

Results

In order to test the hypothesis that rBCG strains expressing a higher level of recombinant malaria surface antigen PfMSP1-19 will be more immunogenic in mice, the PfMSP1-19 gene sequence was cloned into a mycobacterium expression vector under the control of various mycobacterial promoters including hsp60, mtrA, 18 kD, α-Ag, and aceA. PfMSP1-19 was also expressed and directed to different locations within and associated with the rBCG bacilli including intracellular, secretory, and surface locales. The codons of the PfMSP1-19 gene were also changed from the wildtype malaria sequence that is AT-rich to GC-rich. The expression was highest in rBCG expressing GC-rich PfMSP1-19 gene under the control of α-Ag on the cell surface of the mycobacteria among the constructs tested (Table 1).

TABLE 1

Recombinant BCG expressing PfMSP1-19 from AT-rich and GC-rich gene sequences.

| PROMOTER | S.S | Plasmid | Expression | Antibody |
|---|---|---|---|---|
| AT-RICH | | | | |
| hsp |  | 94 | − | − |
| hsp | 19 KD | 95 | + | − |
| hsp | a-Ag | 96 | − | − |
| mtrA |  | 97 | − | − |
| mtrA | 19 KD | 98 | + | − |
| mtrA | a-Ag | 99 | − | − |
| 18 kD |  | 100 | − | − |
| 18 kD | 19 KD | 101 | − | − |
| 18 kD | a-Ag | 102 | + | ++ |
| aceA |  | 103 | − | − |
| aceA | 19 KD | 104 | − | − |
| aceA | a-Ag | 105 | − | − |
| Pa—Ag | a-Ag | 106 | − | − |
| P19 kD | 19 KD | 107 | − | − |
| amd |  | 108 | − | − |
| amd | 19 KD | 109 | − | − |
| amd | a-Ag | 110 | − | − |
| Pa—Ag |  | *121 | − | − |
| Pa—Ag | 19 KD | 122 | + | − |
| Pa—Ag | a-Ag | 123 | − | − |
| P19 kD |  | *125 | − | − |
| P19 kD | 19 KD | 126 | − | − |
| P19 kD | a-Ag | 127 | − | − |
| GC-RICH | | | | |
| hsp | 19 KD | 135 | ++++ | ++++ |
| hsp |  | 136 | + | − |
| hsp | a-Ag | 137 | − | − |
| mtrA | 19 KD | 140 | ++ | +++ |
| mtrA |  | 141 | − | − |
| mtrA | a-Ag | 142 | − | − |
| 18 kD | 19 KD | 143 | ++ | − |
| 18 kD |  | 144 | − | − |
| 18 kD | a-Ag | 145 | − | − |
| aceA | 19 KD | 146 | − | − |
| aceA |  | 147 | − | − |
| aceA | a-Ag | 148 | − | − |
| Pa—Ag | a-Ag | 158 | − | − |
| P19 kD | 19 KD | 159 | − | − |
| amd | 19 KD | 149 | + | − |
| amd |  | 150 | − | − |
| amd | a-Ag | 151 | − | − |
| Pa—Ag | 19 KD | 152 | +++++ | +++++ |
| Pa—Ag |  | 153 | + | − |
| Pa—Ag | a-Ag | 154 | + | − |
| P19 kD | 19 KD | 155 | − | ++ |
| P19 kD |  | 156 | − | − |
| P19 kD | a-Ag | 157 | − | − |

The ability of these rBCG strains to generate antibody response in Balb/c mice was then tested. A correlation between the level of antibody generated in mice immunized with rBCG and the amount of protein expressed in rBCG was found (FIG. 1 and Table 1). rBCG (B152) expressed the highest level of PfMSP1-19 and induced the highest level of antibody response in Balb/c mice. In subsequent studies, we tested the immunogenicity of rBCG (B152) in different strains of mice including Balb/c, C57B/L 6, C3H, and Swiss mice.

Figure 2:
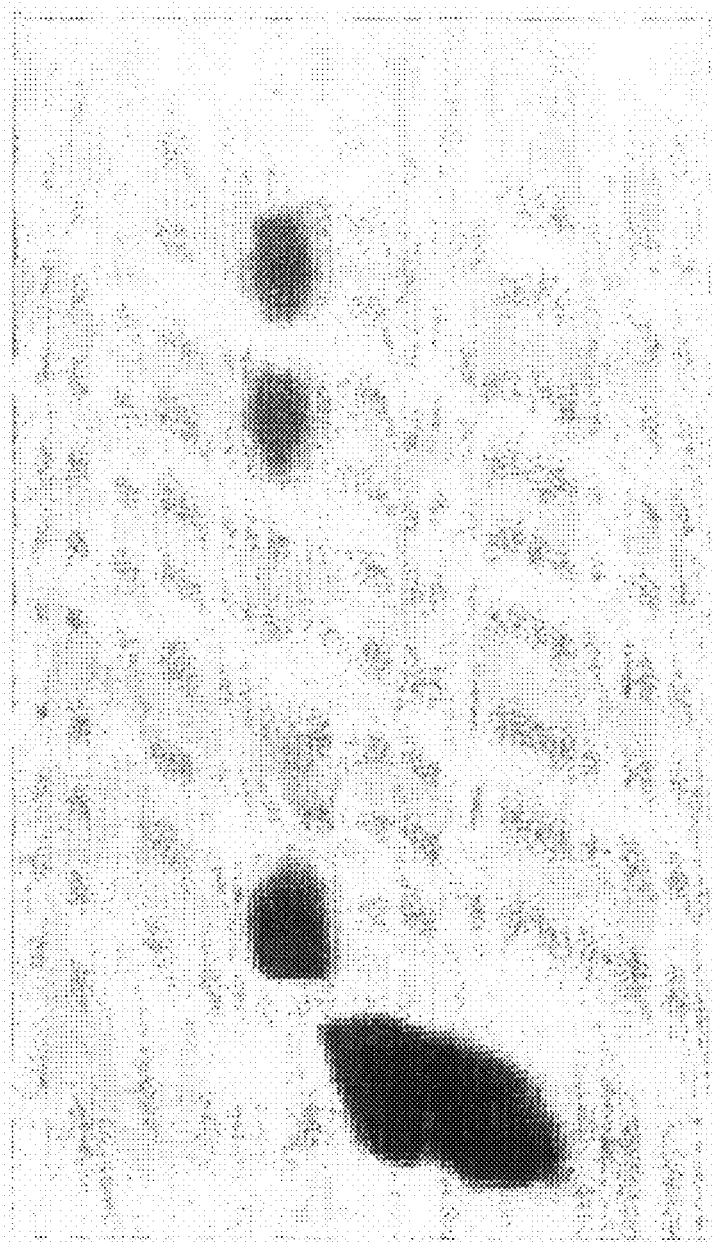
FIG. 2 is a blot showing the expression of PfMSP1-19:: P2P30 in rBCG.

P2P30 T cell epitopes from tetanus toxin have been reported to act as adjuvant that enhances the T cell response in mice when it was fused to various antigens (Panina-Bordignon et al., 1989). The hypothesis that P2P30 universal T cells epitopes enhances the T cells response to malaria surface antigen PfMSP1-19 was tested in mice. The epitope sequences in the 3' end of the malaria antigen PfMSP1-19 gene was cloned. The expression of the fusion protein in rBCG (B103) appeared to be equivalent to that of rBCG (B152) without the epitope (FIG. 2).

Figure 3:
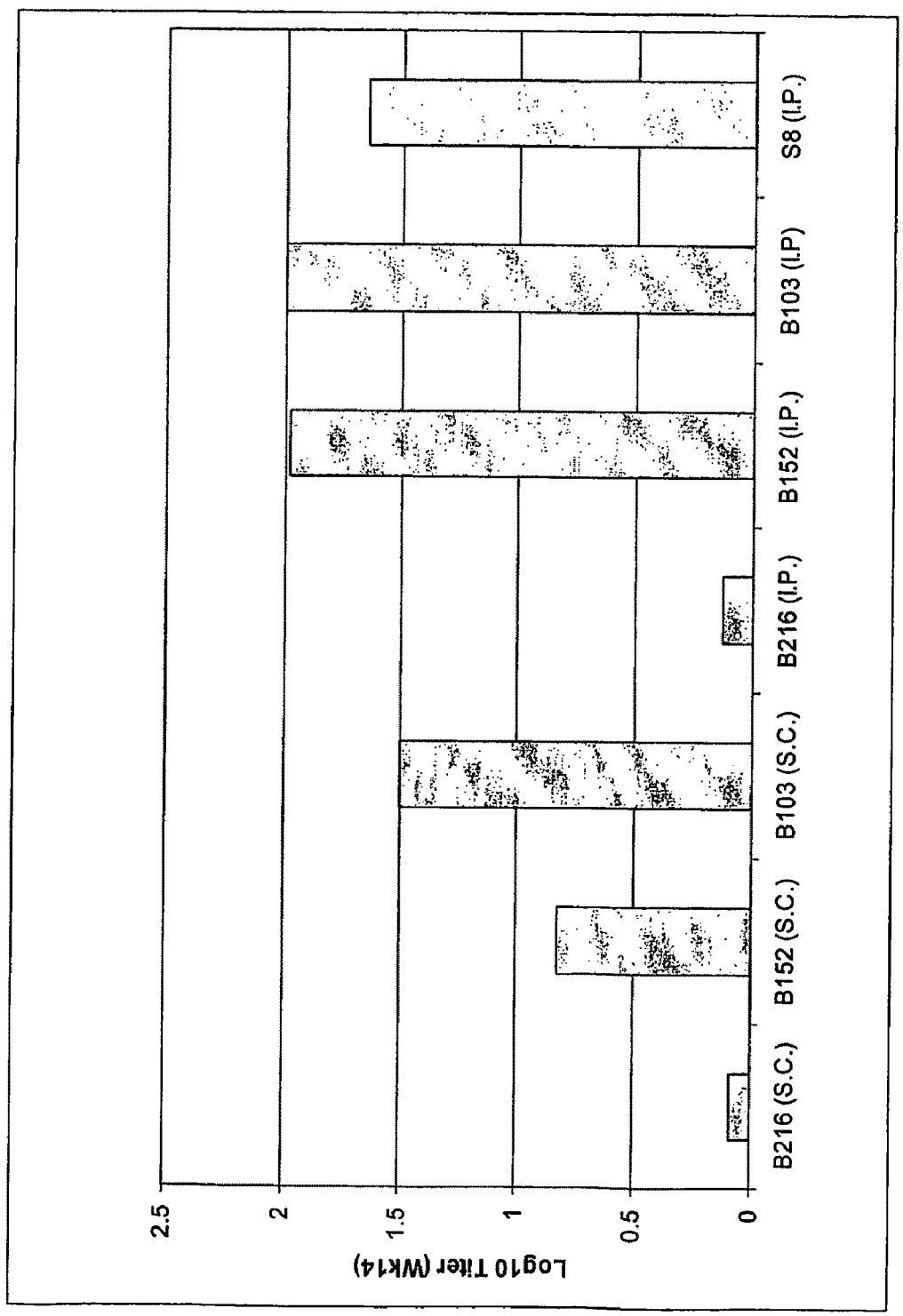
FIG. 3 is a graph showing the antibody response in Balb/c mice immunized with rBCG expressing PfMSP1-19.

The effect of P2P30 T cell epitopes for its immunogenicity in mice by immunizing Balb/c mice with rBCG (B103) subcutaneously or intraperitoneally was first tested. The blood samples were collected at 14 weeks post immunization. The level of antibody against bv-PfMSP1-42 was then measured. Fourteen (14) weeks after immunization, the antibody level of serum from mice immunized with rBCG (B152) was significantly higher than mice immunized with control BCG carrying only empty vector rBCG (B216), though intraperitoneal route of immunization seemed to induce more antibody response than subcutaneous route, confirming earlier observations. While rBCG (B103) also induced significant antibody response in mice, the presence of P30P2 epitopes did not seem to enhance the antibody response to PfMSP1-42 antigen. The immunogenicity of recombinant *M. smegmatis* expressing very high level of PfMSP1-19 (see recombinant *M. smegmatis* S8) was also compared to those of recombinant BCG. Interestingly, at week 14, mice receiving the same dose of recombinant *M. smegmatis* generated a similar level of antibody to those mice receiving rBCG (B152) (FIG. 3).

Figure 4:
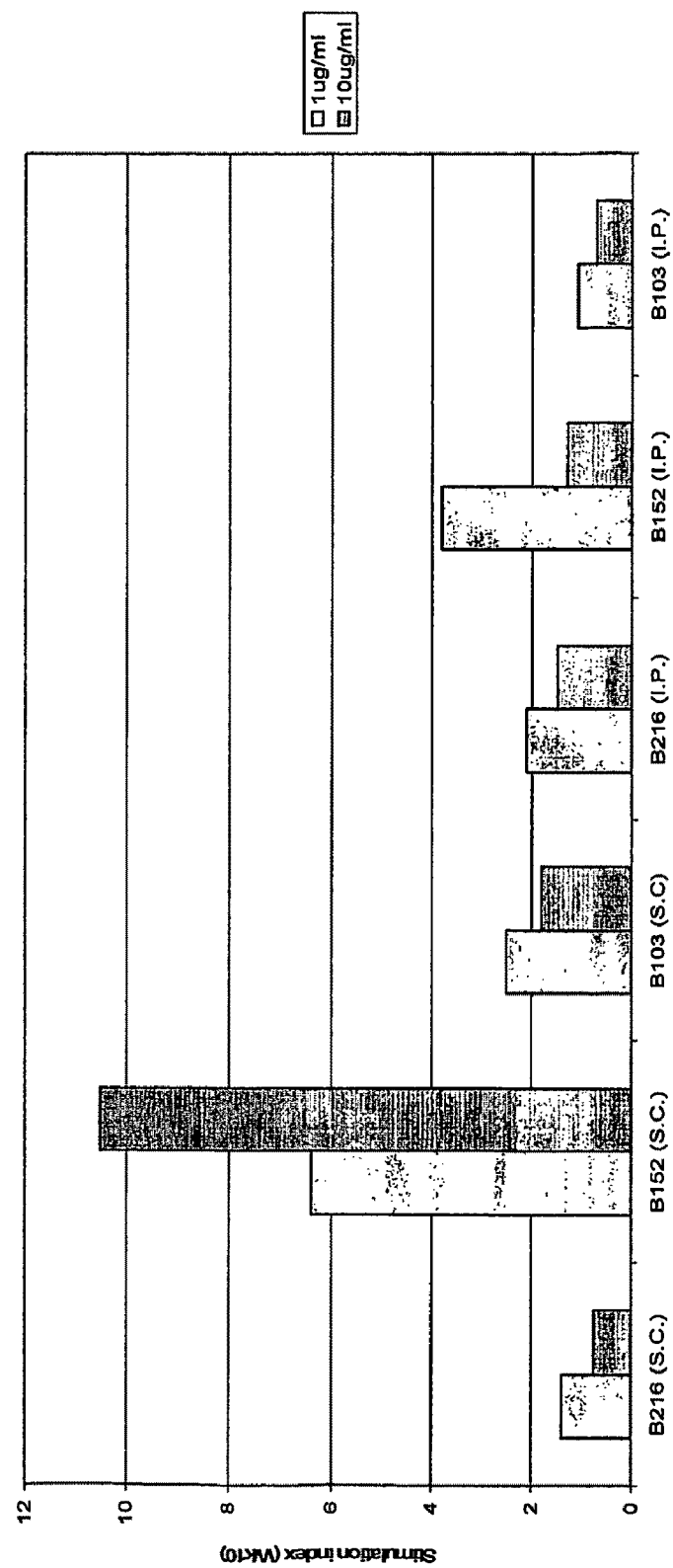
FIG. 4 is a graph showing the T cell response in Balb/c mice immunized with rBCG expressing PfMSP1-19.
Figure 5:
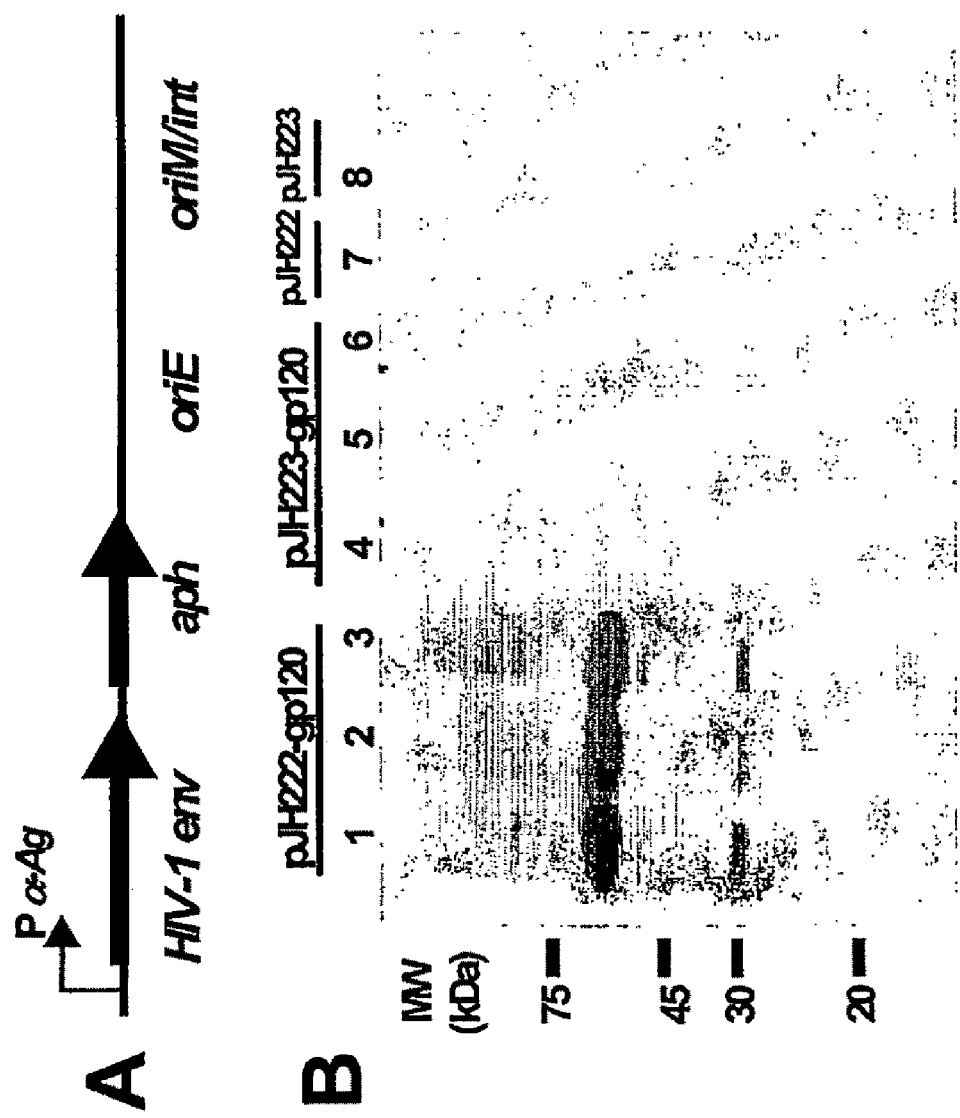
FIG. 5 is a vector diagram and a photograph of a western blot that shows the expression of HIV-1 HXBc2 gp120 envelope in the non-pathogenic *Mycobacterium smegmatis*. Panel A is a diagram showing a codon-optimized HXBc2 gp120 env that was cloned into the *E. coli*/mycobacteria shuttle plasmids pJH222 (multicopy) and pJH223 (integrative). The gp120 env in the plasmids is under the *M. tuberculosis* (Mtb) α-Ag promoter. A fusion protein was created in which the *M. tuberculosis* 19-kDa signal sequence was at the N-terminus and an influenza hemagglutinin epitope (HA) tag was at the C-terminus of the gp120 Env. Both plasmids contained the Tn903-derived aph gene conferring kanamycin-resistance as a selectable marker, and an *E. coli* origin of replication (oriE). The origin of replication (oriM) was inserted into the pJH222 plasmid, while the attP site and the int gene of mycobacteriophage L5 were included in pJH223. Panel B shows the results of a western blot analysis showed expression of the gp120 protein in recombinant *M. smegmatis* MC$^2$155. The gp120 expression of three independent clones of mycobacteria transformed with either pJH222-gp120 (lanes 1-3) or pJH223-gp120 (lanes 4-6) was determined using an anti-HA mAb (clone 3F10). Mycobacteria transformed with either mock pJH222 or pJH223 containing an irrelevant gene (malaria msp1) were utilized as negative controls (lanes 7 and 8).
Figure 6:
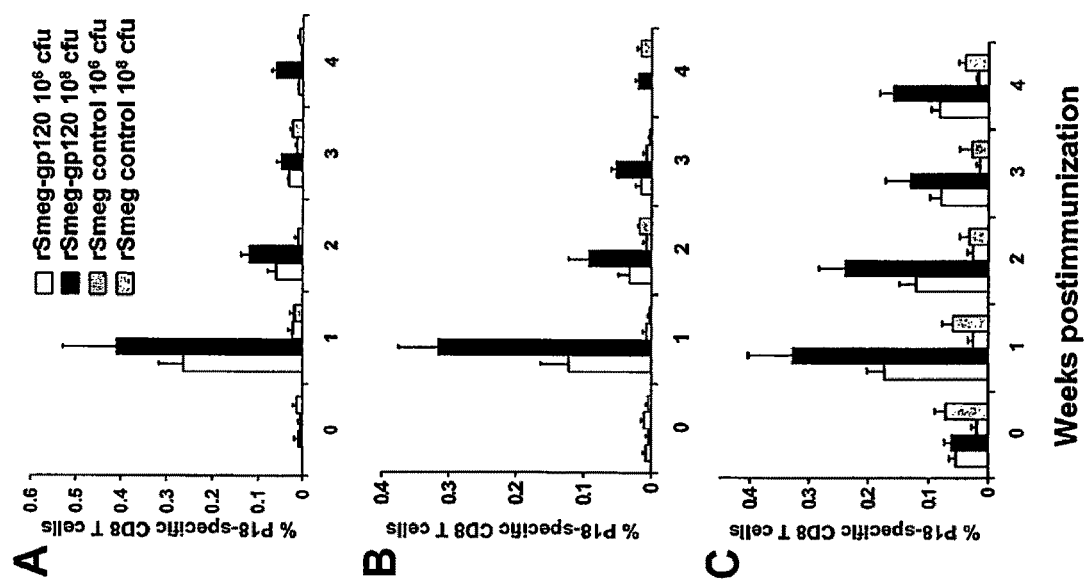
FIG. 6 is graphs of experimental results showing that recombinant *M. smegmatis* elicited HIV-1-specific CD8 T-cell responses in mice. Balb/c mice were inoculated via the intraperitoneal route with approximately $10^6$ CFU or $10^8$ CFU gp120-expressing recombinant *M. smegmatis* (rSmeg-gp120) transformed with either the integrative pJH223-gp120 plasmid (Panel A) or the multi-copy pJH222-gp120 (Panel B). As a negative control, mice were inoculated with the same dose of mycobacteria transformed with the control pJH222- and pJH223-msp1 plasmids (rSmeg control) (Panel C). Mice were inoculated twice (ten weeks apart) with the same dose of either the rSmeg-gp120 (integrative) construct or the rSmeg control. The mean (±SEM) percent HIV-1 HXBc2 gp120 p18-tetramer positive CD8 T cells from PBMC collected at the indicated time points are shown for each group of mice (n=4 per group).
Figure 7A:
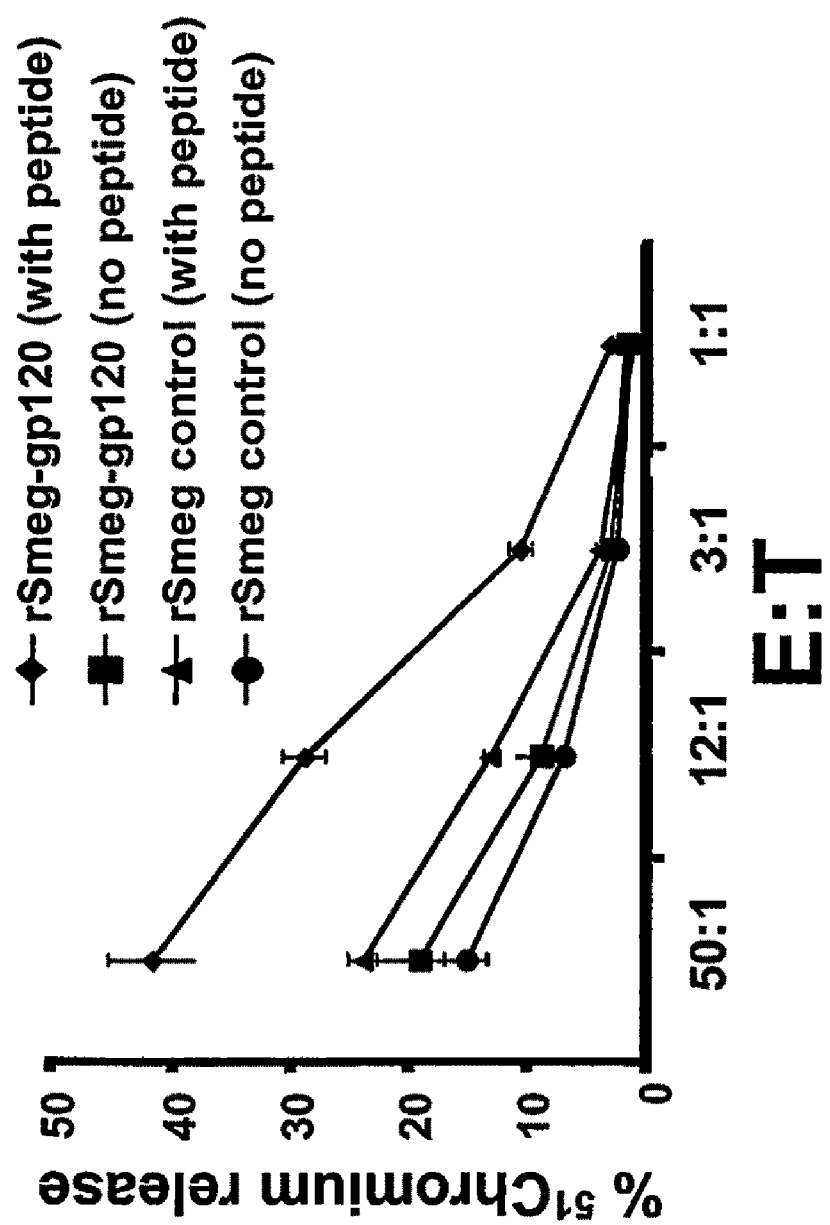
FIG. 7 is graphs showing in vitro function of HIV-specific CD8 T cells primed by r*M. smegmatis*. Panel A is a graph showing cytotoxic activity of HIV-1-specific CD8+ T cells elicited by r*M. smegmatis* immunization. HIV-1-specific CTL were expanded in vitro by stimulating splenocytes isolated from mice at day 14 after a single inoculation with $10^8$ CFU r*M. smegmatis* expressing gp120 (integrative) with 10 ng/ml p18 peptide in the presence of rat IL-2 for 7 days. Cytotoxic activity of the effector cells for P815 target cells pulsed with or without p18 was assessed in a $^{51}$Chromium release assay. Effector to target (E:T) ratios used in the study are indicated. Panel B is a graph showing r*M. smegmatis*-elicited HIV-1-specific CD8+ T cells secreted IFN-γ. Day 7 splenocytes from mice immunized with $10^7$ CFU recombinant mycobacteria expressing gp120 (integrative) were exposed to no peptide, p18, or a gp120 peptide pool, and evaluated in an ELISPOT assay. Splenocytes from mice immunized with r*M. smegmatis* expressing Msp1 were used as a control. The mean (±SEM) spot-forming cells (SFC) per $10^6$ splenocytes for each group of mice (n=4 per group) is shown.
Figure 7B:
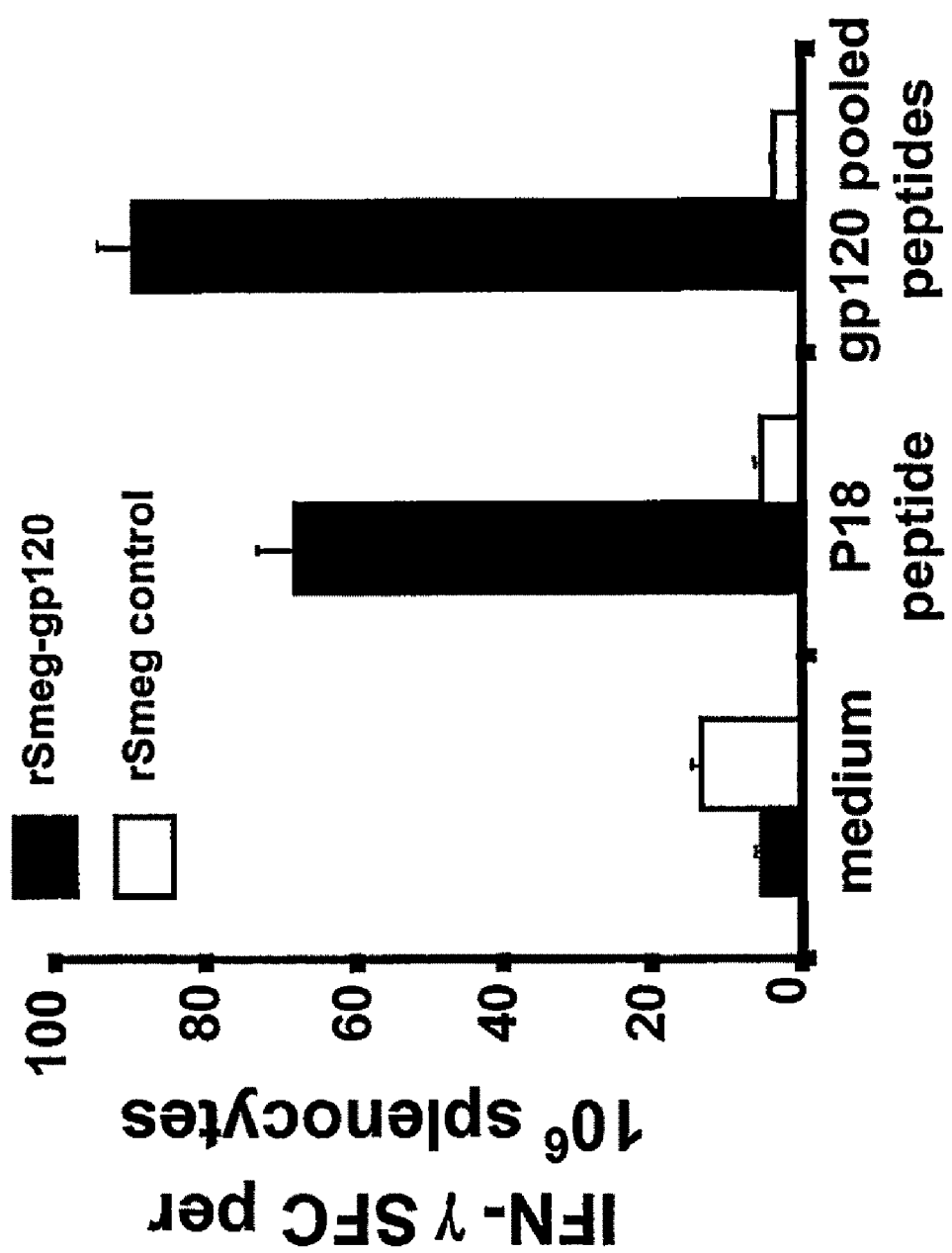

The T cell response in the same groups of mice at 14 weeks post-immunization by T cell proliferation assays was also characterized (FIG. 4). Splenocytes ($2\times10^5$) of three mice from each group were collected and incubated with either 1 or 10 mg of rPfMSP1-19 protein for 2 days and uptake of tritiated thymidine by splenocytes was measured. A Stimulation Index was calculated by dividing the thymidine intake of splenocytes that were stimulated with rPfMSP1-19 protein antigen by splenic cells that were not stimulated. FIG. 3 shows that the T cell response was higher (5-10 fold increase in Stimulation Index) in mice immunized subcutaneously with rBCG expressing PfMSP1-19 (B152) than mice immunized with rBCG carrying empty vector (B216). Subcutaneous immunization of rBCG expressing PfMSP1-19 generated higher T cell response than intraperitoneal immunization. However, P30P2 epitope fusion seemed to have a negative effect on T cell stimulation in mice immunized subcutaneously or intraperitoneally with rBCG expressing PfMSP1-19. Interestingly, at week 21 post immunization, the group of mice receiving recombinant *M. smegmatis* expressing high levels of PfMSP1-19 generated a higher Stimulation Index (2 fold) than mice receiving recombinant BCG expressing PfMSP1-19.

Example 2

Generation of CD8+ T Cell Responses by a Recombinant Nonpathogenic *Mycobacterium smegmatis* Vaccine Vector Expressing HIV-1 Env Example Summary Because the vaccine vectors currently being evaluated in human populations all have significant limitations in their immunogenicity, novel vaccine strategies are needed for the elicitation of cell-mediated immunity. The nonpathogenic, rapidly growing mycobacterium *M. smegmatis* was engineered as a vector expressing full length HIV-1 HXBc2 envelope protein. Immunization of mice with recombinant *M. smegmatis* led to the expansion of MHC class I-restricted HIV-1 epitope-specific CD8+ T cells that were cytolytic and secreted IFN-γ. Effector and memory T lymphocytes (CTL) were elicited, and repeated immunization generated a stable central memory pool of virus-specific cells. Importantly, pre-existing immunity to BCG had only a marginal effect on the immunogenicity of recombinant *M. smegmatis*. This mycobacterium may therefore be a useful vaccine vector.

Materials and Methods

Generation of recombinant mycobacteria. *Mycobacterium smegmatis* MC²155 was grown in Middlebrook 7H9 (Difco) supplemented with 10% ADS and 0.05% Tween 80 (Fisher Scientific). *Mycobacterium bovis* BCG (Pasteur) was grown in 7H9 media supplemented with 10% OADC (Difco) and 0.05% Tween 80. A human codon-optimized HIV-1 IIIB gp120 envelope gene (HXBc2) was cloned into the multi-copy pJH222 and single copy integrative pJH223 *E. coli*/mycobacteria shuttle plasmids. A synthetic operon was constructed containing the viral envelope gene, which is regulated by the *M. tuberculosis* α-antigen promoter and the *M. tuberculosis* 19-kDa signal sequence. For detection of the HIV-1 envelope protein, an HA-tag was fused to the C-terminal end of the envelope. Within the operon, a kanamycin resistance gene was cloned downstream of the viral gene. The multi-copy and integrative plasmids with the HXBc2 envelope gene insert were transformed into the *M. smegmatis* MC²155 strain. Recombinant mycobacterial clones were selected for kanamycin resistance on 7H10 agar containing 20 μg/ml of kanamycin (Sigma). Single colonies were grown in 7H9 medium containing 20 μg/ml of kanamycin and grown by shaking for 2-3 days until an $OD_{600}$ approximately equal to 1. Mycobacteria were then harvested and washed twice in ice cold PBS. Expression of the viral gp120 protein was assessed by Western blotting of mycobacterial lysates (1 μg of total protein) using an anti-HA mAb (clone 3F10) and a chemiluminescence detection kit, according to the manufacturers protocol (Roche Applied Science).

Mice and immunizations. 8-12 week old female Balb/c mice were purchased from Taconic and Charles River laboratories. Mice were housed in a biosafety level 3 facility under specific pathogen-free conditions at the Center for AIDS Research Animal Biohazard Containment Core Suite (Dana-Farber Cancer Institute). Research on mice was approved by the Dana-Farber Cancer Institute Animal Care and Use Committee. Recombinant *M. smegmatis* and BCG were grown in 7H9 medium until an $OD_{600}$ approximately equal to 1. We estimated that bacterial growth to an OD value of 1 is equal to $5\times10^8$ colony-forming units (CFU). For r*M. smegmatis* immunizations, approximately $10^6$ or $10^8$ CFU bacilli were injected via the intraperitoneal route (i.p.) in 200 μl of sterile PBS, 0.02% Tween. Approximately $10^6$ CFU bacilli were injected subcutaneously (s.c.) for BCG immunization.

Tetramer staining and flow cytometric analysis. H-2D$^d$ tetrameric complexes folded with the P18-peptide (RG-PGRAFVTI) (Takahashi et al., 1992), a sequence found in the V3 loop of HIV-1 HXBc2 envelope protein, was prepared as described previously (Staats et al., 2001). Mice were anesthetized with Isoflurane and bled retro-orbitally. Blood was collected in RPMI 1640 containing 40 U of heparin (American Pharmaceutical Partners) per ml. Peripheral blood mononuclear cells (PBMCs) were isolated using lympholyte-M (Cedarlane) and stained with the P18-tetramer conjugated with phycoerythrin (PE) and anti-CD8α mAb (Ly-2; Caltag) conjugated with allophycocyanin (APC) to detect P18-specific CD8+ T cells. The cells were washed in PBS containing 2% fetal bovine serum (FBS) and fixed with PBS containing 2% formaldehyde (Polysciences). CD8+ T cells were analyzed for tetramer staining using two-color flow cytometry on a FACS Array (BD Pharmingen). For phenotyping the P18-specific CD8+ T cells, splenocytes and PBMC were sampled one week after immunization of mice with recombinant mycobacteria and stained with anti-CD8α mAb (53-6.7; BD Pharmingen) conjugated with PerCP-Cy5.5, anti-CD62L mAb (MEL-14; BD Pharmingen) conjugated with APC, anti-CD44 mAb (IM-7; eBiosciences) conjugated with APC-Cy7, anti-CD127 mAb (A7R34; eBiosciences) conjugated with PE-Cy7, and the P18-tetramer conjugated with PE. Multi-color flow analysis was performed using the BD LSRII Cytometer (BD Biosciences) and the FlowJo software (Tree Star).

$^{51}$Chromium release assay. Splenocytes were harvested from mice one week after immunization with $10^7$ CFU recombinant mycobacteria. The cells were resuspended in RPMI 1640 containing 10% FBS, and cultured in a 24-well plate ($8\times10^6$/well) with 10 ng of p18 epitope peptide per ml.

IL-2 (Sigma) was added to cultures on day 2 to a final concentration of 10 U/ml. On day 7, cells were harvested, washed once, and used as effectors in a $^{51}$Cr release assay with P815 target cells (American Type Culture Collection). P815 cells were cultured overnight in the presence of medium alone or with 100 ng of p18 peptide per ml. Cells (2×10$^6$) were labeled with 150 µCi of $^{51}$Cr for 1 h at 37° C., washed twice, and added to a 96-well round-bottom plate at 104/well in 100 µl of 10% RPMI medium. Titrations of effector cells were added to triplicate wells in 100 µl of medium. Lytic activity was assessed in a four-hour 51Cr release assay as previously described (Seaman et al., 2004). Percent specific lysis was calculated as follows: 100×(experimental−spontaneous release)/(maximum−spontaneous release).

IFN-γ ELISPOT assay. An ELISPOT assay was performed to measure IFN-γ production as previously described (Seaman et al., 2004). Briefly, 96-well Multiscreen HA plates (Millipore) were coated by overnight incubation (100 µl/well) at 4° C. with rat anti-mouse IFN-γ mAb (clone R4-6A2; BD Pharmingen) at 10 µg/ml in PBS. Splenocytes were harvested from individual mice one week after immunization with 10$^7$ CFU recombinant mycobacteria. Effector cells were plated in triplicate at 2×10$^5$/well in a 100-µl final volume with medium alone, 4 µg of p18 epitope peptide per ml, or 4 µg of Env peptide pool per ml. The pool consisted of 47 overlapping 15-mer peptides spanning the HIV-1 IIIB gp120 protein (Centralized Facility for AIDS Reagents, Potters Bar, United Kingdom) and was used such that each peptide was present at a concentration of 4 µg/ml. After a 24 h incubation at 37° C., the plates were washed free of cells with PBS-0.05% Tween 20 and incubated overnight at 4° C. with 100 µl of biotinylated rat anti-mouse IFN-γ mAb (clone XMG1.2; BD Pharmingen) per well at 5 µg/ml. Plates were washed four times, and 75 µl of streptavidin-alkaline phosphatase (Southern Biotechnology Associates) was added at a 1/500 dilution. After a 2 h incubation, plates were washed four times and developed with Nitro Blue Tetrazolium-5-bromo-4-chloro-3-indolylphosphate chromogen (Pierce). Plates were analyzed with an ELISPOT reader (Hitech Instruments).

Statistical analysis. Data were expressed as mean±SEM. Statistical tests were performed using Student's t test. A P value less than 0.05 was considered significant.

Results

Figure 8:
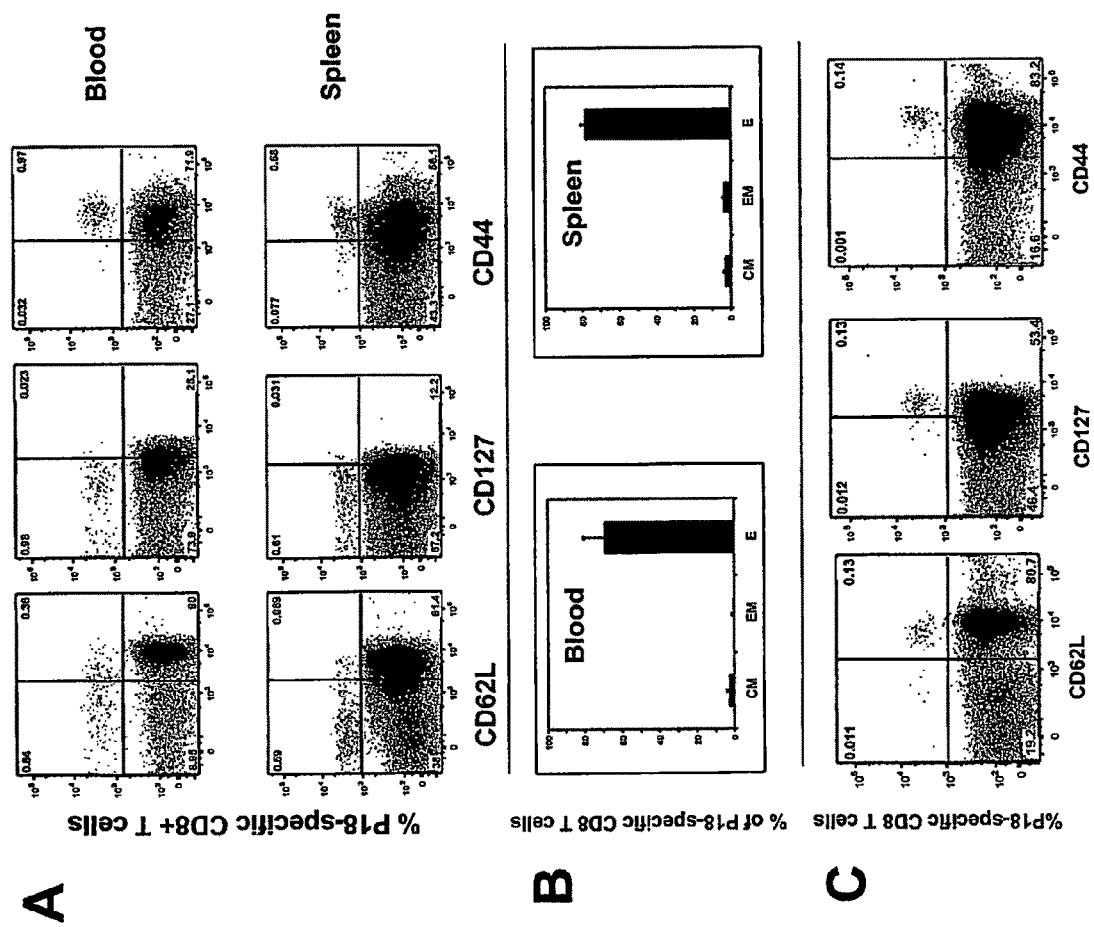
FIG. 8 is graphs showing the phenotype of HIV-1-specific CD8 T cells elicited by immunization with r*M. smegmatis*. Mice were immunized with $10^8$ CFU r*M. smegmatis* expressing gp120 (integrative). Panel A shows a flow cytometric analysis of week one PBMC and splenocytes from immunized mice revealed expression of CD44 on the surface of all r*M. smegmatis*-elicited tetramer+ cells. CD62L and CD127 were expressed on a subset of the tetramer+ cells. Panel B shows the proportions of effector (P18-tetramer+, CD127−, and CD62L$^{lo}$), effector memory (P18-tetramer+, CD127+, and CD62L$^{lo}$), and central memory (P18-tetramer+, CD127+, and CD62L$^{hi}$) cells in the blood and spleen of mice immunized with r*M. smegmatis*. Effector, effector memory, and central memory cells are denoted as E, EM, and CM, respectively. The mean (±SEM) percent E, EM or CM for each group of mice (n=4 per group) is shown. Panel C shows that peripheral blood HIV-1-specific CD8+ T cells from mice one year after immunization with r*M. smegmatis* expressing gp120 were predominantly central memory cells. PBMC were pooled from 4 mice that were inoculated twice (ten weeks apart) with $10^8$ CFU bacilli.
Figure 9:
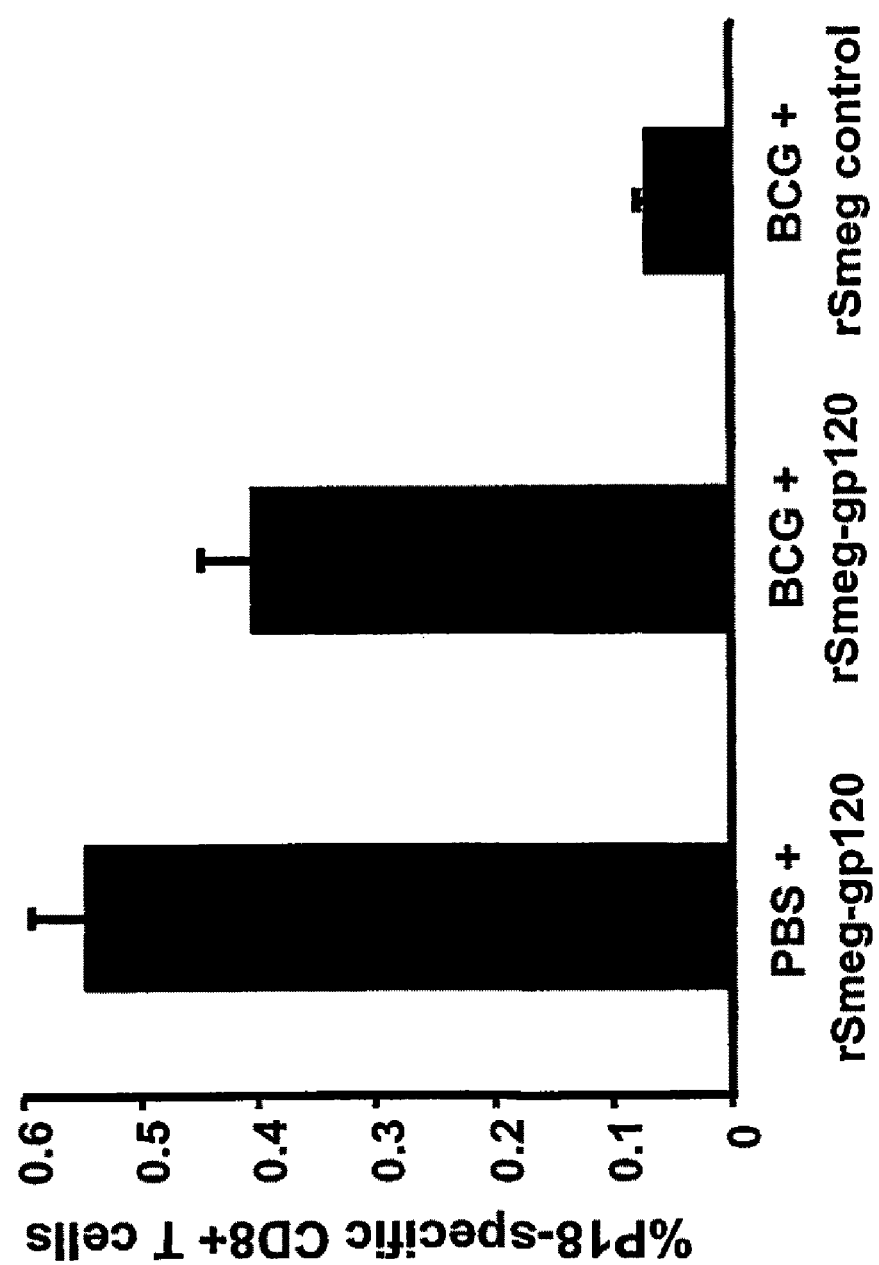
FIG. 9 is a graph showing that recombinant *M. smegmatis*-elicited HIV-1-specific CD8+ T cell responses in mice pre-immunized with BCG. Mice were immunized with wildtype BCG (Pasteur) or PBS and six months later with $10^8$ CFU r*M. smegmatis* expressing gp120 (integrative) (indicated as BCG+rSmeg-gp120 and PBS+rSmeg-gp120, respectively). BCG-pre-immunized mice that were subsequently inoculated with rSmeg control were used as a negative control (indicated as BCG+rSmeg control). Tetramer analysis was performed on the PBMC of mice one week after inoculation with the r*M. smegmatis* constructs. The mean (±SEM) percent of HIV-1 HXBc2 gp120 P18-tetramer positive CD8+ T cells is shown for each group (n=4-5 mice per group).
Figure 10:
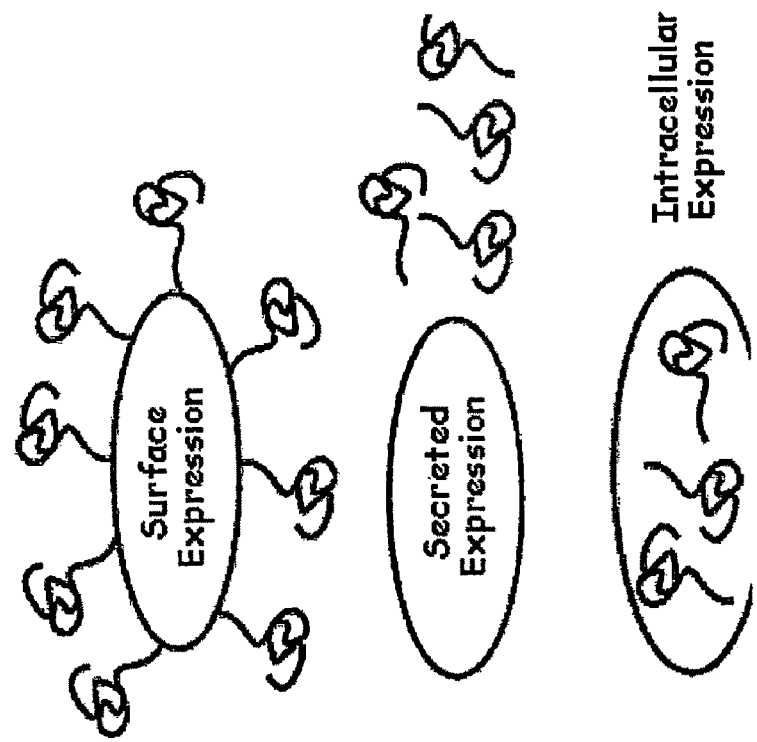
FIG. 10 is a cartoon showing the strategy to express HIV env in BCG or attenuated MTB.
Figure 11:
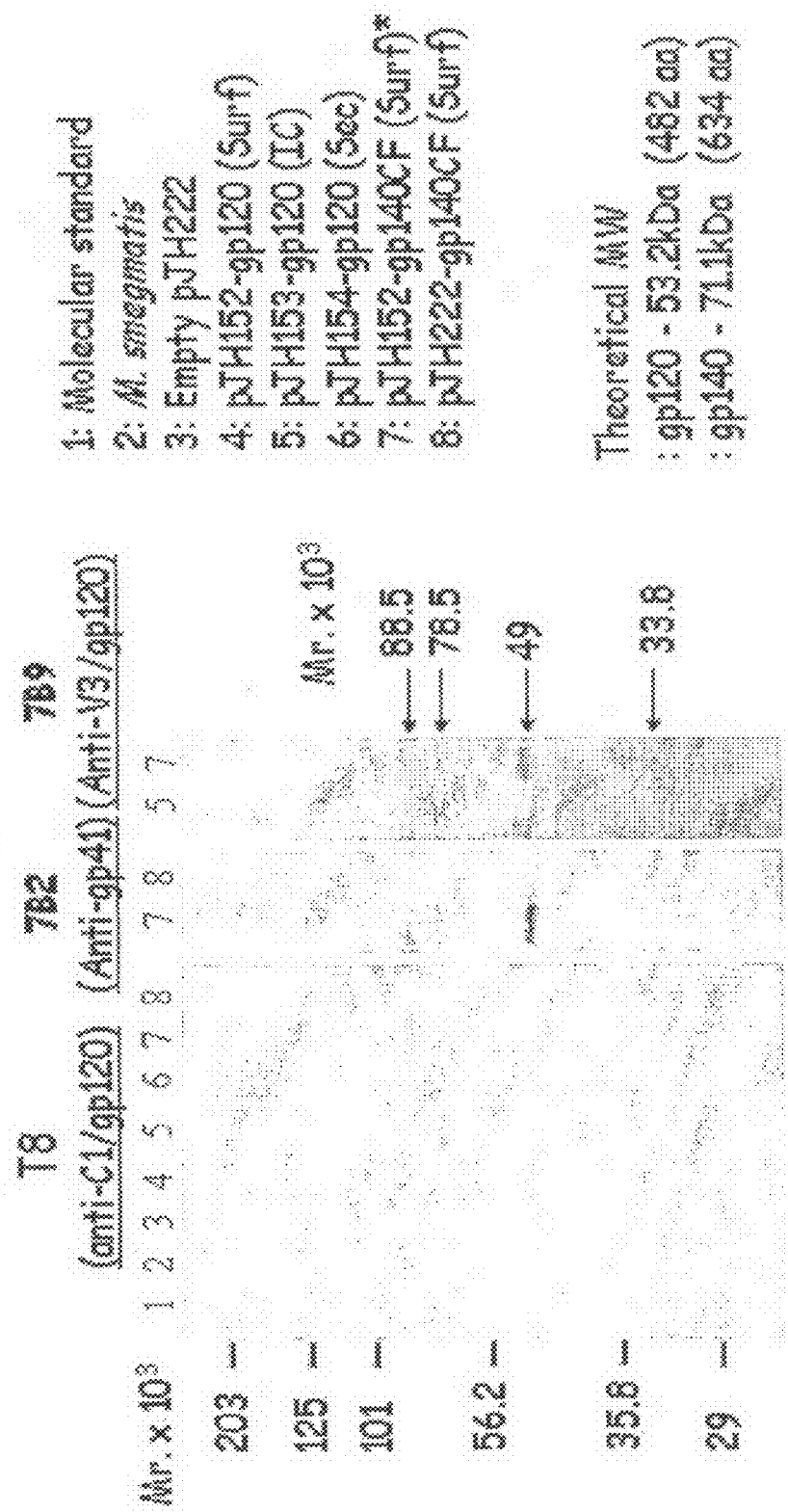
FIG. 11 is a blot showing the expression of HIV-1 CON6-gp120 and CON6-gp140CF envelope proteins in *M. smegmatis*. The expression of intact CON6 gp120 was demonstrated in *M. smegmatis* transformed by the surface expression plasmid of pJH152 (lane 4), the intracellular expression plasmid of pJH153 (lane 5), and the secreted expression plasmid of pJH154 (lane 6). The expression of CON6 gp140CF was also performed in *M. smegmatis* transformed by the surface expression plasmids such as pJH152 (lane 7) and pJH222 (lane 8). Both the intact and partially cleaved gp140 products were shown as demonstrated using gp120 mab T8 (anti-C1 gp120 region), gp41 specific mab 7B2, and V3-loop specific 7B9. Theoretical molecular mass based on amino acids sequences of CON6 gp120 without glycosylation is approximately 53 and CON6 gp140CF is 71 kDa. However, the protein band of CON6 gp120 and CON6 gp140CF expressed in *M. smegmatis* is approximately 70 kDa and 80 kDa, respectively. This suggested that the expression of both CON6 gp120 and CON6 gp140CF in *M. smegmatis* is only partially glycosylated.
Figure 12:
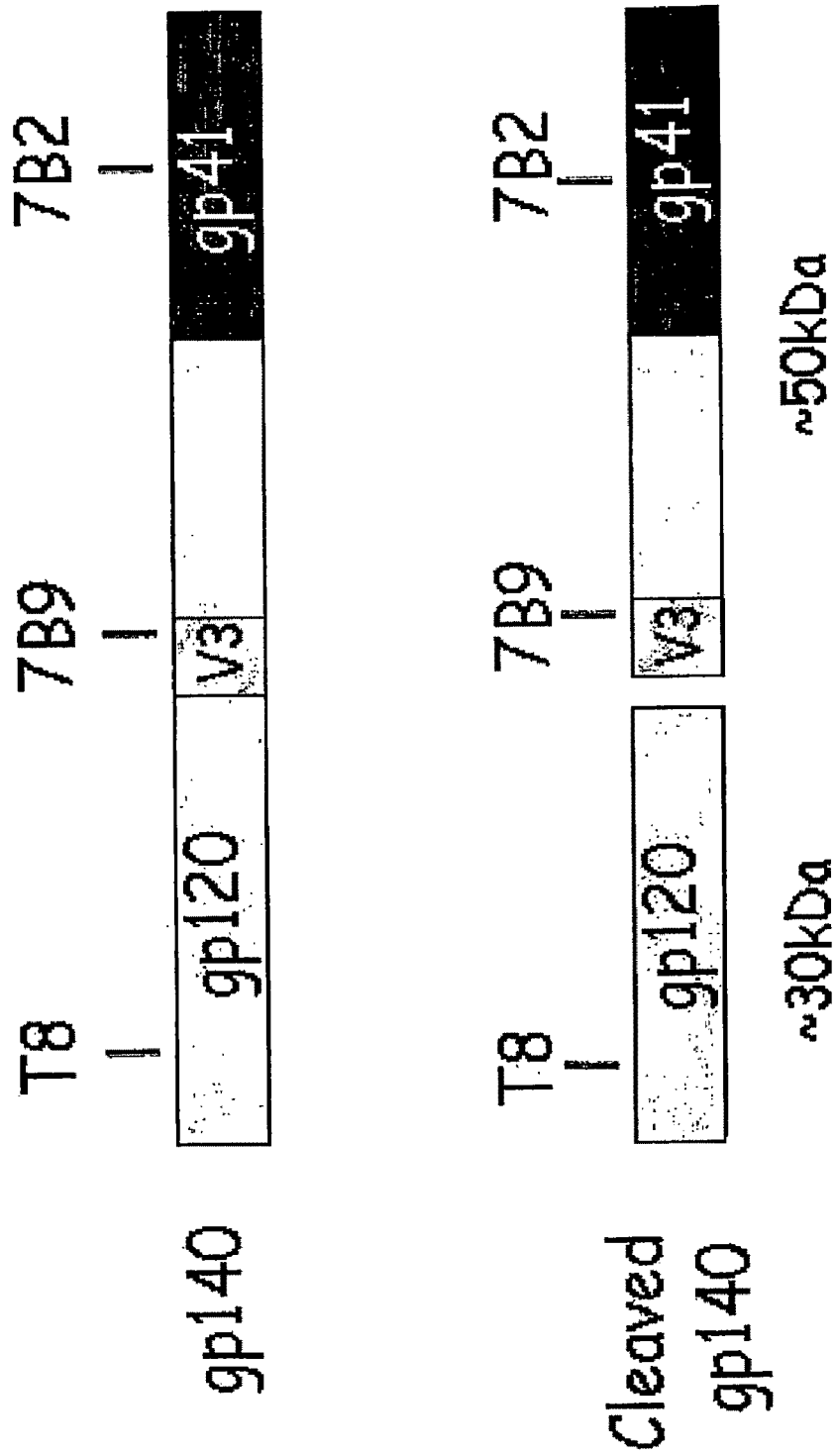
FIG. 12 is a graphic showing the binding location of HIV-1 Mabs on HIV-1 CON6 envelope proteins. The figure shows the full-length gp140 and its reacting sites of T8, 7B2, and 7B9. However, in the cleaved gp140, 30 kDa peptide only reacts with T8 while 50 kda peptide reacts with both 7B2 and 7B9. Thus this data suggests that 50 kDa cleaved peptide contains V3-loop region and gp41.
Figure 13:
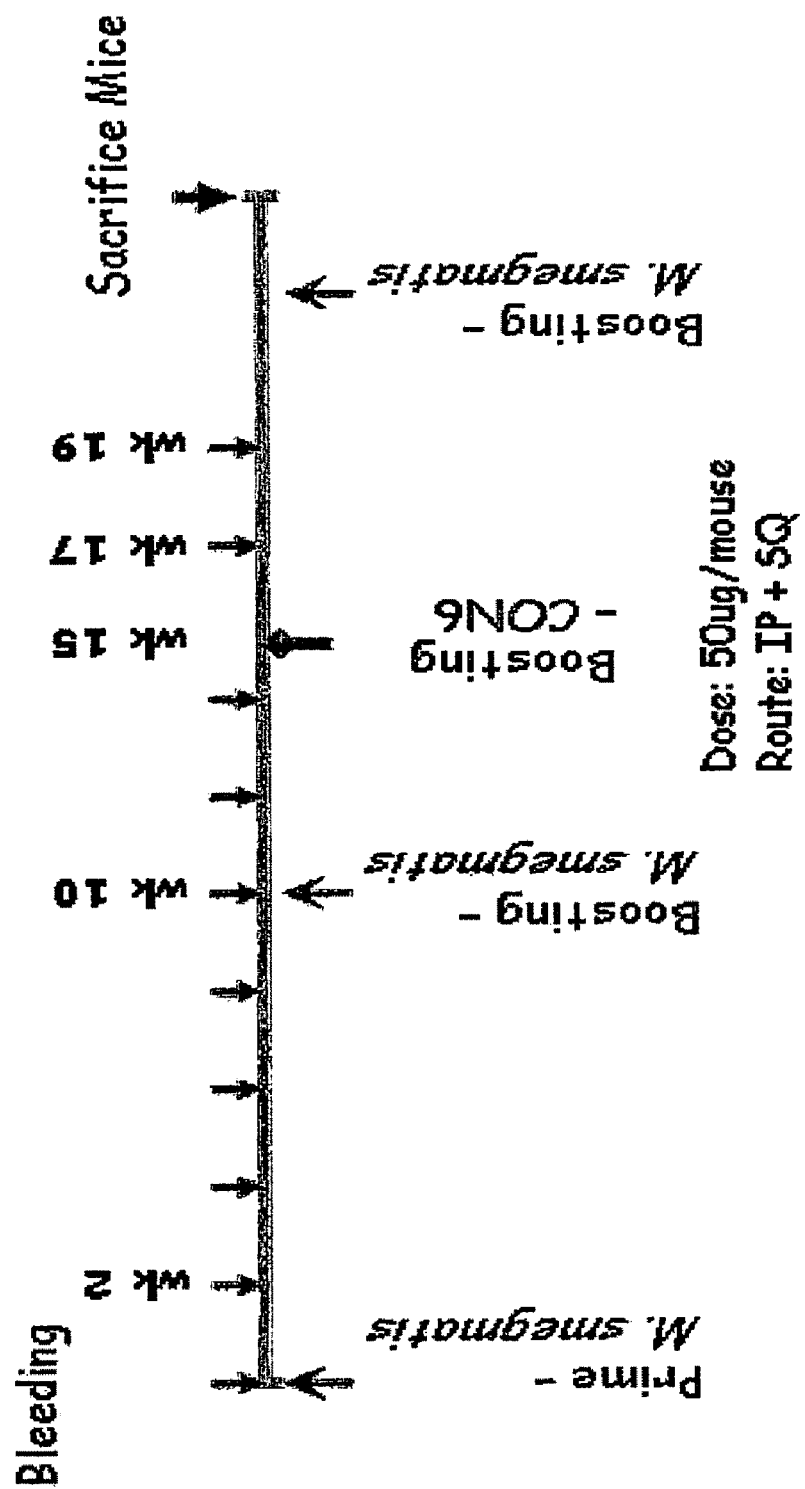
FIG. 13 shows the r-*M. smegmatis* immunization schedule in mice. We set up total 60 group of mouse immunization study with *M. smegmatis* and HIV ENV constructs in mycobacterial with 5 mice per group. Mice were immunized 8 different immunogens by the two different injection route: intraperitoneal (IP) vs intradermal (ID). The immunogens were such as controls (*M. smegmatis*, Empty pJH222/*M. smegmatis*), HIV envelope gp120 (pJH152-gp120/*M. smegmatis*, pJH153-gp120/*M. smegmatis*, pJH154-gp120/*M. smegmatis*), and HIV envelope gp140CF (pJH152-gp140CF/*M. smegmatis*, pJH222/*M. smegmatis*, pJH154-gp140CF/*M. smegmatis*). Each immunogen was immunized with four different dosage groups such as $10^{10}$ CFU, $10^9$ CFU, $10^8$ CFU, and $10^7$ CFU. After the initial immunization, we have bled mice every two weeks and antibodies responses were monitored by ELISA. Boosting with the same immunogens was done in week 10 and with CON6-gp140CF in week 15.
Figure 14:
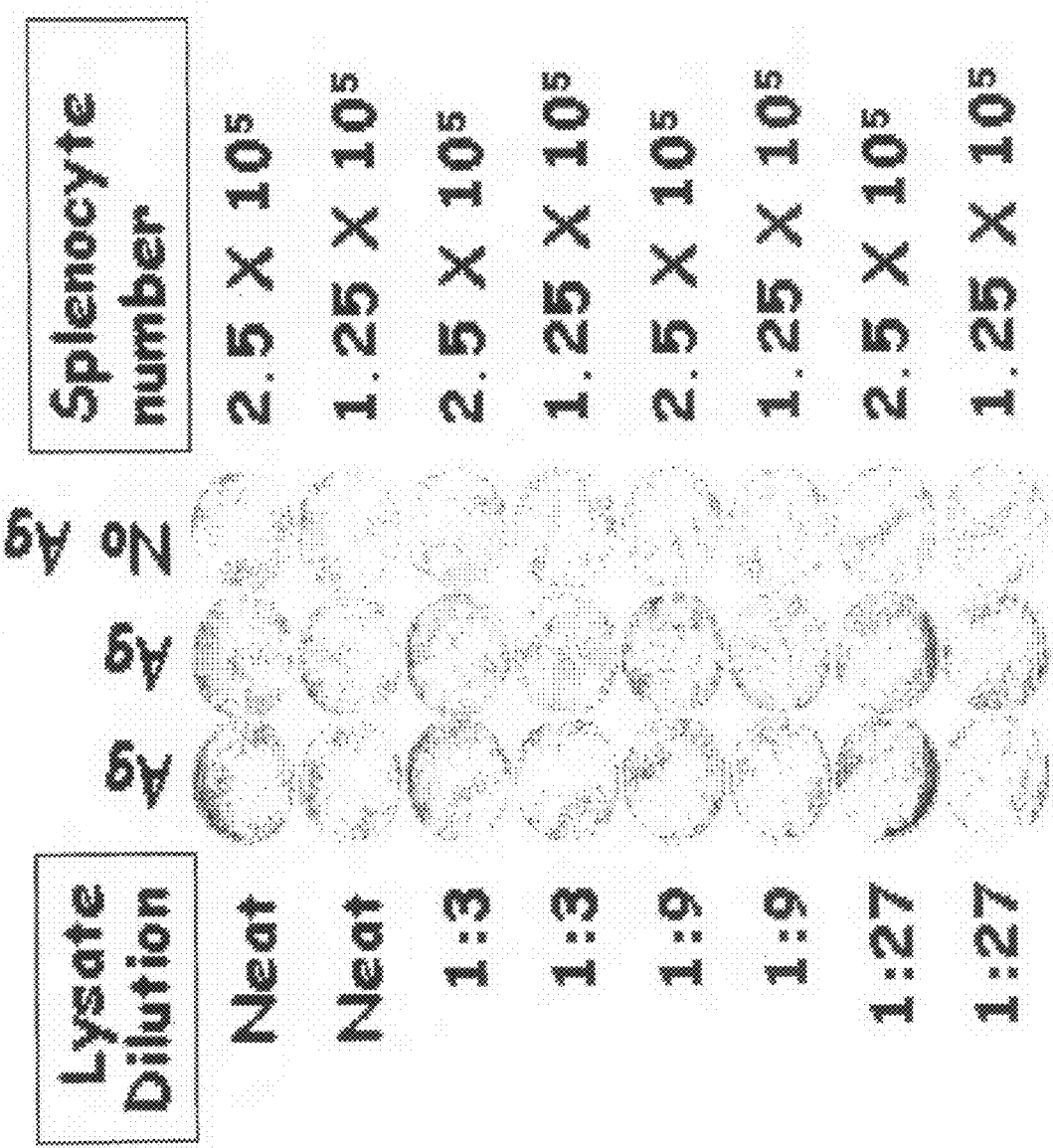
FIG. 14 shows ELISPOT wells after stimulation with MTB whole cell lysate or saline. Mice were single IP injection of $10^9$ CFU pJH152-gp140CF/*M. smegmatis*. After two weeks 1P immunization, harvest mice spleens for IFNγ ELISPOT using native MTB antigens from NIAID-funded reagent program at Colorado State University.
Figure 15:
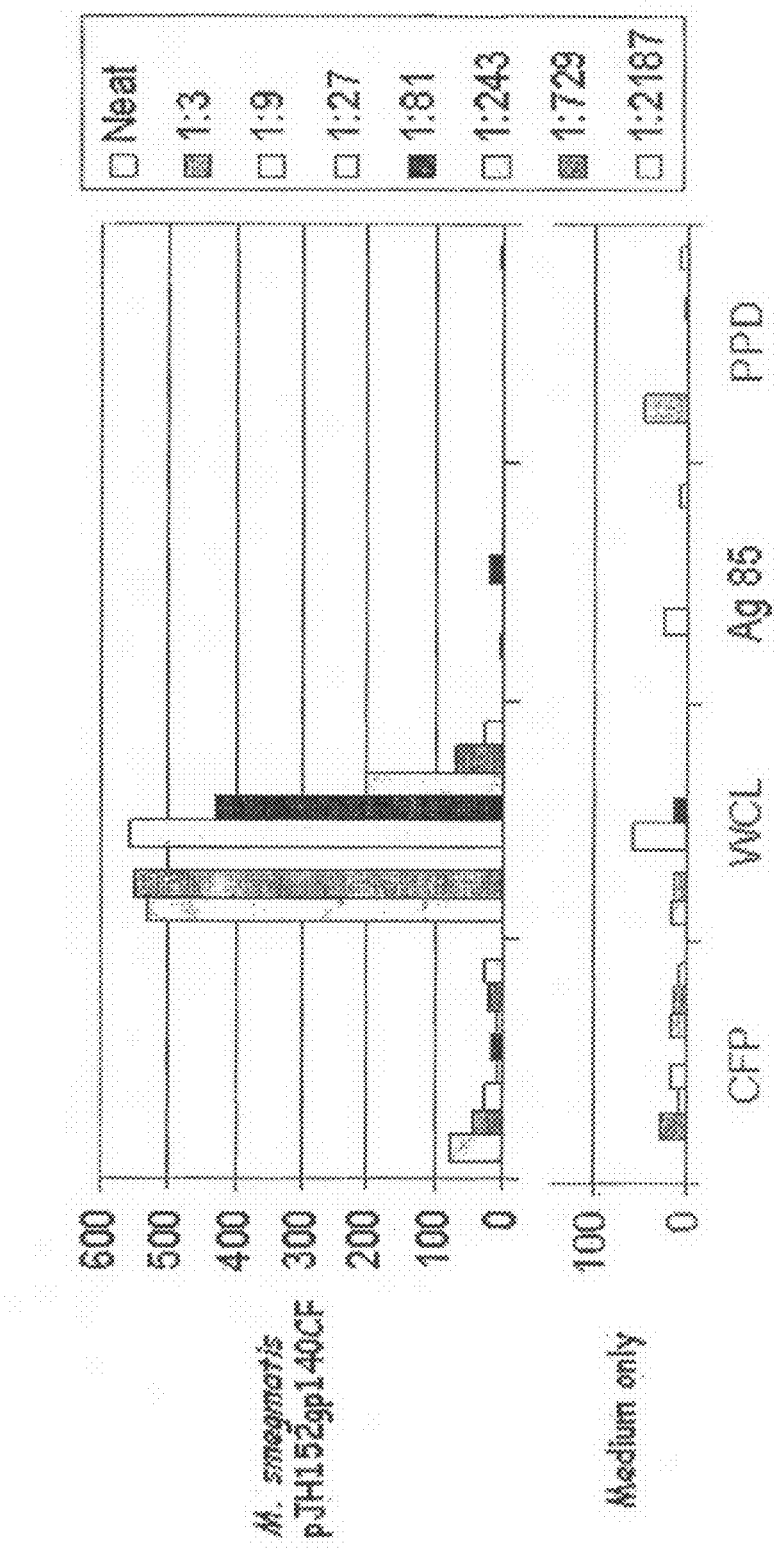
FIG. 15 is a graph of mycobacterial antigen-specific IFNγ spot-forming cells after a single IP inoculation with recombinant *M. smegmatis* or medium. This figure shows MTB WCL could be better choice for IFNγ ELISPOT rather than MTB CFP, MTB antigen 85, or PPD. (Native mycobacterial antigens: CFP, culture filtrate protein; WCL, whole cell lysate; Ag 85, antigen 85 complex; PPD, purified protein derivative.
Figure 16:
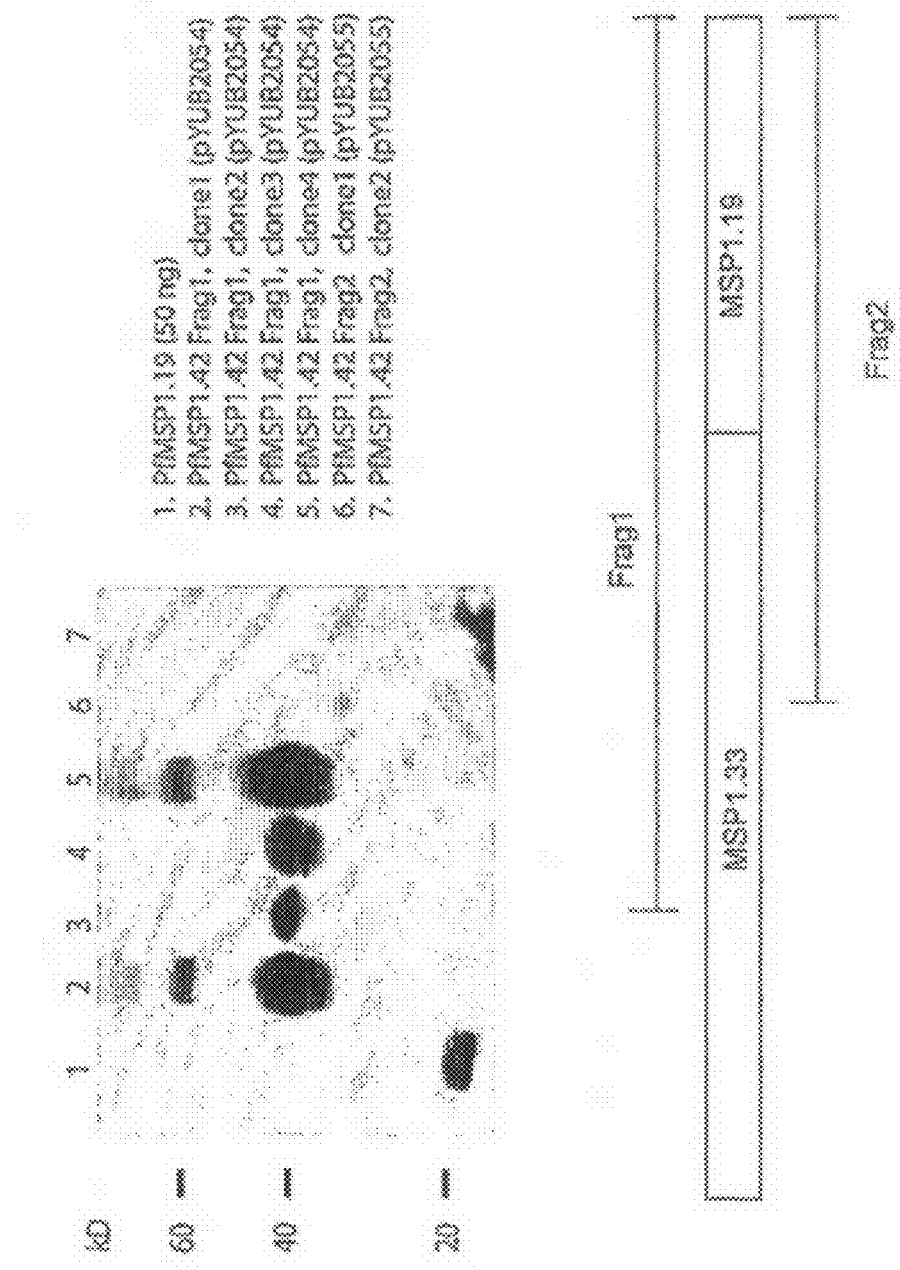
FIG. 16 is a western blot and a diagram showing amounts of malaria antigen produced by various *M. smegmatis* clones having plasmid constructs containing one of two fragments of the *P. falciparum* MSP antigen gene.
Figure 17:
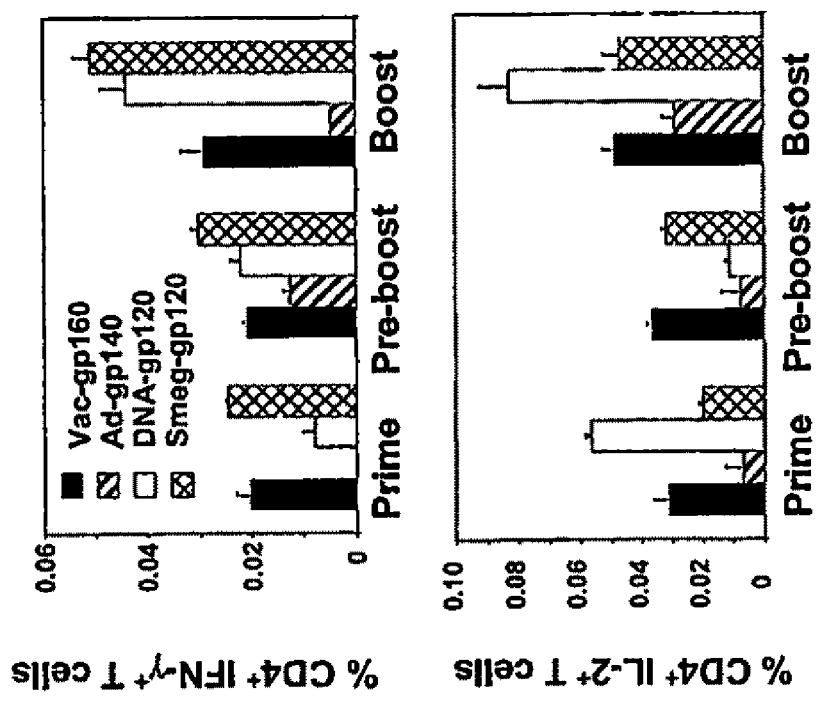
FIG. 17 is graphs showing cytokine expression by gp120-specific CD4+ T cells. Mice were immunized with Smeg-gp120 ($5 \times 10^7$ CFU), Vac-gp160 ($2 \times 10^7$ PFU), Ad-gp140 ($2 \times 10^7$ particles) or DNA-gp120 (50 μg) and 10 weeks later were boosted with the same quantity of vector used for priming. Splenocytes were harvested one week (Vac-gp160 and Smeg-gp120) or two weeks (Ad-gp140 and DNA-gp120) after the prime and boost immunization, or 10 weeks after the prime immunization (pre-boost). The cells were cultured for 6 hr in the presence of medium alone or a pool of 47 overlapping peptides spanning the HIV-1 IIIB gp120 protein (2 μg/ml). Data are presented as the percentages of CD4+ IFN-γ+ and CD4+ IL-2+ T cells following peptide stimulation and represent the means of five mice per group ±SE.

Generation of recombinant *Mycobacterium smegmatis* expressing HIV-1 gp120 envelope protein. The pJH222 and pJH223 *E. coli*/mycobacteria shuttle plasmids were used to express a HIV-1 HXBc2 env gene codon optimized for human cell expression. A human codon-optimized HIV-1 env was used since the codons used by human cells are similar to those used by mycobacteria (Andersson and Scharp, 1996; de Miranda et al., 2000; Pan et al., 1998). pJH222 is a multi-copy plasmid that replicates episomally in mycobacteria (Snapper et al., 1988); the pJH223 is an integration-proficient plasmid (Lee et al., 1991) that integrates as a single-copy DNA in the mycobacterial genome (FIG. 5A). Both plasmids contained the *M. tuberculosis* α antigen promoter to drive expression of HXBc2 env. The HIV-1 protein was fused to an HA tag at the C-terminus. The N-terminus of the HIV-1 envelope was fused to the 19-kDa signal sequence to facilitate expression of the viral protein in the mycobacterial membrane. Fusion with the 19-kDa signal sequence has been shown to increase immunogenicity of a heterologous protein (Stover et al., 1991).

Both env-containing plasmids were transformed into the efficient plasmid transformation mutant *M. smegmatis* $MC^2155$ (Snapper et al., 1988). Western blot analysis using an anti-HA mAb showed that recombinant *M. smegmatis* clones transformed with the multi-copy plasmid had higher expression levels of the viral protein than those transformed with the integrating plasmid (FIG. 5B). Control r*M. smegmatis* constructs, which were transformed with either the pJH222 or pJH223 containing the malaria msp1 gene, did not express the viral antigen. The predicted molecular weight of the envelope protein expressed by the r*M. smegmatis* constructs suggested an absence of the heavy glycosylation seen in the mature gp120 envelope of HIV-1 (Wyatt et al., 1998). These results show the successful expression of the full-length HIV-1 gp120 protein in the rapidly growing, nonpathogenic *M. smegmatis*.

r*M. smegmatis* immunization elicited functional HIV-1-specific CD8+ T cells. While BCG and *Mycobacterium vaccae* (Hetzel et al., 1998) have been assessed as potential vaccine vectors, other nonpathogenic species of mycobacteria have not been evaluated for this application. We therefore tested the r*M. smegmatis* constructs for their immunogenicity in mice. Immune responses were monitored in Balb/c mice using a tetramer assay, measuring CD8+ T cell responses to the H-$2D^d$-restricted P18 epitope from the V3 loop of the HXBc2 envelope protein. Both the multi-copy and the single copy r*M. smegmatis* constructs expressing gp120 elicited peripheral blood HIV-specific CD8+ T cell responses in mice immunized intraperitoneally with either $10^6$ or $10^8$ CFU bacilli (P<0.05 versus control groups at weeks one, two, and three post-immunization) (FIGS. 6A and 6B). Higher frequency responses were seen in mice immunized with $10^8$ CFU than those immunized with $10^6$ CFU bacilli. Interestingly, despite significantly lower viral antigen expression by r*M. smegmatis* containing the highly stable single copy plasmid than r*M. smegmatis* containing the multi-copy plasmid (FIG. 5B), the magnitudes of the immune responses elicited by both constructs were comparable. CD8+ T cell responses peaked at week 1, rapidly declined thereafter, and were undetectable in the peripheral blood by week 4.

Mice were inoculated with r*M. smegmatis* expressing gp120 twice, at an interval of 10-weeks, to determine whether the T cell responses could be boosted. P18-specific responses increased in magnitude, and were seen one week after immunization (P<0.05 versus control groups). However, these peak responses were not greater than those seen following a single inoculation (FIG. 6C). Responses in the boosted mice declined thereafter, but remained detectable even one year following the initial immunization (data not shown). These results demonstrate that r*M. smegmatis* is capable of eliciting MHC class I-restricted CD8+ T cells specific for the HIV-1 envelope.

The functional capacity of the r*M. smegmatis*-induced HIV-1 envelope-specific CD8+ T cells was then determined. Splenocytes were harvested one week after immunization of mice with $10^7$ CFU of the single-copy r*M. smegmatis* construct and evaluated in IFN-γ ELISPOT and $^{51}Cr$-release assays. The splenocytes secreted IFN-γ after overnight stimulation with the dominant CD8+ T cell P18 epitope peptide or a pool of overlapping peptides spanning the entire gp120 protein (P<0.001 versus control groups) (FIG. 7B). The cytotoxic activity of the r*M. smegmatis*-elicited CD8+ T cells was also assessed. Splenocytes were stimulated with the P18-peptide for one week in the presence of IL-2 and evaluated as effector cells in a $^{51}Cr$-release assay. These effector cells were able to kill efficiently P815 target cells pulsed with the P18 peptide (P<0.01 versus control groups at E:T ratios 50:1, 12:1 and 3:1) (FIG. 7A). Thus, the r*M. smegmatis*-elicited HIV-1-specific CD8+ T cells were capable of secreting IFN-γ and mediating cytolytic activity in response to HIV-1 envelope peptide stimulation.

rM. smegmatis immunization elicited both effector and memory HIV-1 Env-specific CD8+ T cells. To further characterize the rM. smegmatis-induced CD8+ T cells, we evaluated these Env-specific T cells for their state of maturation and functional commitment by assessing their expression of CD62L, CD127 and CD44 using surface staining with monoclonal antibodies and flow cytometric analysis. Tetramer+ CD8+ T cells were found in both the spleen and the peripheral blood one week after immunization with rM. smegmatis expressing gp120. In contrast, HIV-1-specific CD8+ T cells were not generated in mice immunized with the control mycobacteria construct. All the tetramer+ CD8 cells expressed CD44, indicating that they were activated (FIG. 8A). Moreover, the majority of these CD8 T cells were effector cells (tetramer+, $CD44^{hi}$, CD127−, and $CD62L^{lo}$), and a small proportion was either effector memory (tetramer+, $CD44^{hi}$, CD127+, and $CD62L^{lo}$) or central memory cells (tetramer+, $CD44^{hi}$, CD127+, and $CD62L^{lo}$). This was seen both in the peripheral blood and spleen of the immunized mice (FIG. 8B). One year after immunization with rM. smegmatis, essentially all of the peripheral blood tetramer+ CD8+ T cells were central memory cells (FIG. 8C). These data indicate that rM. smegmatis can generate effector, effector memory and long-lived central memory HIV-specific CD8+ T cells.

rM. smegmatis elicited HIV-1 Env-specific CD8+ T cells in BCG immune mice. A large proportion of the human population has received BCG as a tuberculosis vaccine, and we were concerned that prior BCG exposure might substantially blunt the immunogenicity of a rM. smegmatis vaccine. Whether anti-BCG immunity can affect the immunogenicity of rM. smegmatis constructs was therefore evaluated in mice. To induce anti-BCG immunity, mice were inoculated with $10^6$ CFU wildtype BCG or PBS and 6 months later were inoculated with rM. smegmatis expressing gp120 (Gheorghiu et al., 1994). In fact, only a modest reduction in peak CD8+ tetramer+responses were observed in the BCG-preimmunized mice (FIG. 9). These results suggest that pre-existing immunity to BCG may have only a marginal effect on the immunogenicity of rM. smegmatis.

Discussion

A novel vaccine vector is described here. The vector is a recombinant nonpathogenic *Mycobacterium smegmatis* $MC^2155$ (rM. smegmatis) expressing the entire HIV-1 HXBc2 gp120 envelope protein, which was immunogenic in mice. The strain $mc^2155$ is a mutant of M. smegmatis (ATCC 607) that is transformable with pAL5000 plasmids at 7 orders of magnitude higher frequency than the parental strain (Snapper et al., 1990). The efficient plasmid transformation phenotype has caused $mc^2155$ to be the surrogate host of choice for the analysis of genes from pathogenic mycobacteria (Converse and Cox, 2005; de Mendonca-Lima, 2001; Wei et al., 2000) and has recently been sequenced by TIGR. Moreover, this strain has been shown to be nonpathogenic following intravenous infections of SCID mice (Bange et al., 1999). We evaluated a variety of mycobacterial promoters and regulatory genes and found that the use of M. tuberculosis α antigen promoter and fusion of the transgene with the 19-kDa signal sequence optimized the immunogenicity of the vaccine construct. A number of factors probably contributed to this increased immunogenicity. This configuration clearly enhanced the expression of the HIV-1 gp120 envelope protein in mycobacteria (data not shown). Furthermore, fusion of the gp120 protein with the 19-kDa protein may have created a chimeric lipoprotein that is immunogenic, perhaps because of acylation of the signal sequence (Young and Garbe, 1991). The acylated moiety was found to be important for MHC class I antigen presentation of lipoproteins, perhaps because it facilitates lipoprotein interaction with the Toll-like receptor 2 (TLR2) (Grode et al., 2002; Neyrolles et al., 2001).

It is interesting to speculate that the immunogenicity of the HIV-1 envelope 19-kDa fusion lipoprotein in the rapidly growing non-pathogenic rM. smegmatis mycobacteria may be associated with the inability of this recombinant vector to persist. Although lipoproteins are certainly immunogenic, persistent exposure to lipoproteins can lead to suppression of antigen presentation by macrophages (Noss et al., 2001; Tobian et al., 2003). Both M. bovis BCG and M. tuberculosis can persist in host cells and inhibit phagosome maturation (Via et al., 1997; 1998. Persisting M. tuberculosis and BCG may exert immunosuppressive effects through ligation of lipoproteins to TLRs localized to the phagosome (Ahmad-Nejad et al., 2002; Ozinsky et al., 2000; Pai et al., 2004; Tobian et al., 2003; Underhill et al., 1999). On the other hand, M. smegmatis does not inhibit phagosome maturation and is degraded rapidly by phagolysosomal proteases. An explanation for the robust immunogenicity of the rM. smegmatis constructs will likely come from parallel studies of the immunogenicity of the HIV envelope chimeric lipoprotein in rBCG and rM. smegmatis as well as an evaluation of the roles of persistence and lipoprotein-TLR interactions in the generation of CD8+ T cell responses elicited by mycobacteria.

rM. smegmatis-elicited HIV-1-specific CD8+ T cells exhibited effector functions such as cytolysis and production of IFN-γ. The ability of recombinant, nonpathogenic rapidly growing mycobacteria to elicit antigen-specific CTL responses has never been reported previously. However, M. tuberculosis or recombinant M. bovis BCG have been shown to elicit antigen-specific CTL (Aldovini and Young, 1991; Kamath et al., 2004). The ability of HIV-1 vaccine vectors to elicit strong CTL responses is likely to be critical for vaccine-induced immune containment of HIV-1 replication and prevention of AIDS (Letvin, 2002).

Recombinant M. smegmatis was previously assessed as a vaccine in a mouse tumor model (Cheadle et al., 2005). Cheadle et al. showed that M. smegmatis was better than BCG at promoting DC maturation. However, recombinant M. smegmatis expressing a CTL epitope of the OVA antigen did not protect against challenge with a tumor expressing this epitope, whereas BCG expressing the same epitope protected mice against the OVA epitope-expressing tumor (Cheadle et al., 2005). This absence of anti-tumor activity elicited by recombinant M. smegmatis was associated with poor presentation of peptides by the non-pathogenic mycobacteria to an OVA-specific T cell line in vitro (Cheadle et al., 2005). However, since the OVA-specific T cell responses were not measured after immunization with the recombinant mycobacteria in this study, the inability of recombinant M. smegmatis to confer protection against a tumor challenge could not be attributed to inefficient induction of tumor antigen-specific CTL responses in vivo. In contrast to the findings of Cheadle et al. (2005) recombinant M. smegmatis was shown to access the MHC class I pathway better than BCG for presentation of peptide antigens (Neyrolles et al., 2001). Furthermore, a recombinant M. smegmatis expressing TNF-α was shown to have anti-tumor properties in mice (Young et al., 2004). The conflicting findings in these studies may be explained by the nature of the antigen expressed by mycobacteria. Neyrolles et al. (2001) expressed the influenza NP CTL epitope fused to the 19-kDa lipoprotein in mycobacteria. In contrast, Cheadle et al. (2005) expressed a secreted OVA CTL epitope in mycobacteria.

The kinetics of the rM. smegmatis-elicited T cell responses differed from those of T cell responses generated using other vaccine modalities. rM. smegmatis-elicited HIV-specific CD8+ T cell responses were maximal one week after immunization. This peak T cell response is earlier than responses elicited by plasmid DNA, adenoviral vectors and vaccinia vectors, which generally are maximal 10 to 14 days post-immunization (Barouch et al., 2003; Seaman et al., 2004). Interestingly, an early peak immune response has also been described in mice immunized with recombinant Listeria monocytogenes (Kaech and Ahmed (2001). rM. smegmatis also induced peak T cell responses that were of lower magnitude than those induced by recombinant viral vectors, but similar in magnitude to those elicited by plasmid DNA (Seaman et al., 2004).

The maturation and differentiation status of the rM. smegmatis-elicited CD8+ T cells was defined using mAbs specific for CD44, CD62L, and CD127 (Huster et al., 2004). In both the peripheral blood and spleen of rM. smegmatis-immunized mice, the majority of the HIV-specific CTL generated were effector cells ($CD44^{hi}$, CD127−, $CD62L^{lo}$) and very few effector memory ($CD44^{hi}$, CD127+, $CD62L^{lo}$) and central memory ($CD44^{hi}$, CD127+, $CD62L^{lo}$) CTL were seen at the time of peak immune responses. Interestingly, in mice receiving two immunizations with rM. smegmatis, we also found a small but stable population of HIV-1-specific central memory CD8+ T cells. These data therefore suggest that rM. smegmatis is capable of generating both HIV-1-specific effector and memory cells in vivo. The ability of the rM. smegmatis vector to generate central memory cells is particularly important since these cells have been shown to expand in vivo and mediate protective immunity following a challenge with a pathogenic organism (Wherry et al., 2003.

There is growing evidence that vector or pathogen persistence may have an adverse effect on the generation of T cell memory. Persistent LCMV and lentiviral infections result in the generation of T cells that have lost the ability to perform some important effector functions (Appay et al., 2000; Fuller and Zajac, 2003; McKay et al., 2002; Wherry et al., 2003; Zajac et al., 1998). Persistent mycobacterial infections by slow-growing M. tuberculosis and BCG may also adversely affect T cell memory responses. On the other hand, vectors that do not persist can generate good T cell memory (Wherry and Ahmed, 2004). Therefore, the rapidly growing M. smegmatis vector may be better at eliciting memory T cell responses than persistent mycobacterial vectors because M. smegmatis is eliminated rapidly in the host.

Interestingly, we found that the multi-copy and the single copy vectors elicited comparable tetramer responses despite the fact that the multi-copy rM. smegmatis construct expressed significantly more HIV-1 envelope protein. High levels of gp120 expression have been shown to be toxic to mycobacteria (Stover et al., 1993). Consistent with this finding, we observed that the in vitro growth of the multi-copy rM. smegmatis was slower than the single copy vector (data not shown). Moreover, studies have shown that recombinant mycobacteria containing an integrated HIV transgene stably express that transgene and are highly immunogenic (Mederle et al., 2002; Stover et al., 1991). Thus, recombinant mycobacteria with integrated transgenes appear to be useful vaccine vectors.

A major limitation of the clinical utility of a number of vaccine vectors currently in development is the inhibition of vector immunogenicity by pre-existing anti-vector immunity. For example, immunity to the HIV-1 vaccine vector adenovirus serotype 5 (rAd5) has been shown to blunt the immunogenicity of rAd5 vaccines (Barouch et al., 2004; Molnar-Kimber et al., 1998). Since BCG is administered to a large proportion of the human population as a TB vaccine, anti-mycobacterial immunity might diminish the immunogenicity of recombinant mycobacterial vectors such as rM. smegmatis. However, our data indicate that BCG immunity affects the immunogenicity of rM. smegmatis only modestly. Consistent with this observation, it was previously reported that mice immunized with wildtype BCG still developed T cell and antibody responses to the HIV-1 Nef and β-galactosidase transgenes expressed in recombinant BCG (Gheorghiu et al., 1994). Pre-existing immunologic memory responses to BCG could result in the rapid destruction of recombinant M. smegmatis, which might favor cross-priming of the heterologous HIV-1 gp120 antigen (Kaufmann and Schaible, 2005). Hence, recombinant mycobacterial vaccines may be useful in BCG-immunized individuals.

Supplemental data for these studies is provided in Tables 2 and 3 (below) and FIGS. 9-14.

TABLE 2

Summary of Mycobacterial expression plasmids expressing HIV-1 CON6-gp120 or CON6-gp140CF.

| Vectors | Designed for | Marker | Inserts | Cloning sites | Seq. confirmation |
|---|---|---|---|---|---|
| pMV261 | Intracellular expression | Kanamycin | Con6-gp120 & Con6-gp140CF | BamHI/HpaI | Whole inserts: OK |
| pMV361 | Chromosomal intergrated vector | Kanamycin | Con6-gp120 & Con6-gp140CF | EcoRI/HpaI | Whole inserts: OK |
| pJH152 | Surface expression | Kanamycin | Con6-gp120 & Con6-gp140CF | ApaI/HpaI | Junction region: OK |
| pJH153 | Intracellular expression | Kanamycin | Con6-gp120 & Con6-gp140CF | ApaI/HpaI | Junction region: OK |
| pJH154 | Secreted expression | Kanamycin | Con6-gp120 & Con6-gp140CF | ApaI/HpaI | Whole inserts: OK |
| pYUB2051 | Intracellular expression | Hygromycin | Con6-gp120 & Con6-gp140CF | ApaI/HpaI | Junction region: OK |
| pYUB2052 | Surface expression | Hygromycin | Con6-gp120 & Con6-gp140CF | ApaI/HpaI | Junction region: OK |
| pYUB2053 | Secreted expression | Hygromycin | Con6-gp120 & Con6-gp140CF | ApaI/HpaI | Junction region: OK |
| pJH222 | Surface expression | Kanamycin | Con6-gp140CF | NdeI/SpeI | Junction region: OK |

Figure 18:
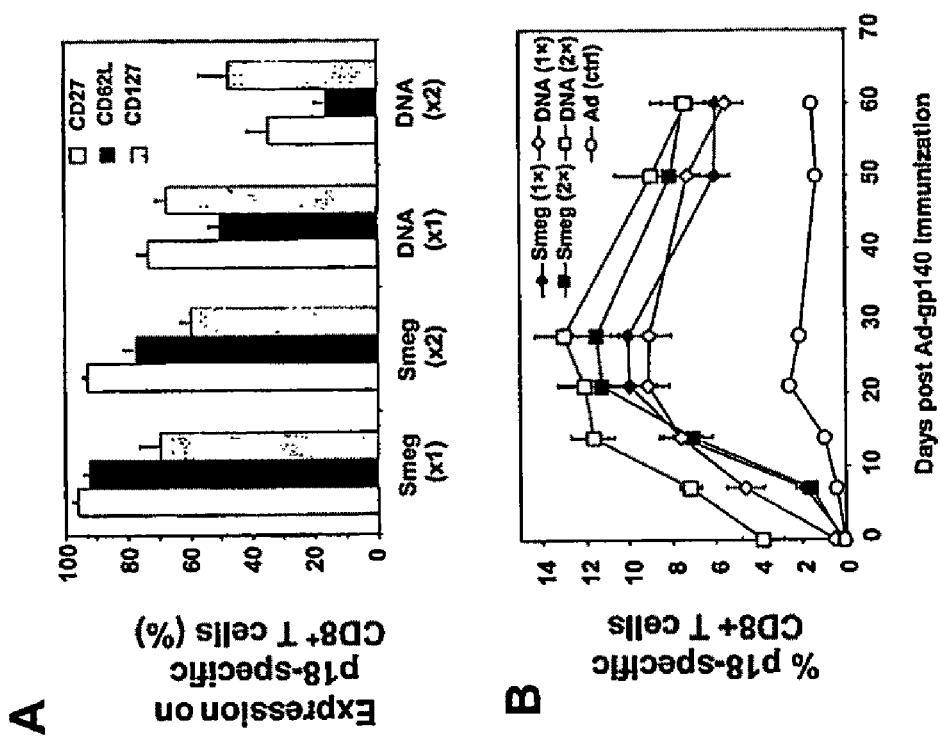
FIG. 18 is graphs showing results from heterologous prime-boost immunization using Smeg-gp120 or DNA-gp120 followed by Ad-gp140. Mice were immunized with Smeg-gp120 ($5 \times 10^7$ CFU) or DNA-gp120 (50 μg) and 10 weeks later some mice were similarly immunized a second time. Panel A shows expression of CD62L, CD127 and CD27 on p18-specific CD8+ T cells 20 weeks after the first immunization (×1) and 10 weeks after the second immunization (×2). Panel B shows the kinetics of p18-specific CD8+ T cells in Smeg-gp120 and DNA-gp120 immunized mice (prime and boost) following heterologous immunization with $10^6$ particles of Ad-gp140. Data represent the mean of 5-10 mice per group ±SE.

This table shows a summary of mycobacterial plasmids expressing HIV-1 CON6-gp120 or CON6-gp140CF that have been made. pMV261 is a constitutive expression vector and pMV361 is a coincident increase in Hsp60-fusion protein in response to stress with heat, acid, and peroxide. pJH vectors have kanamycin resistant marker and designed to deliver expressed proteins in different localization: pJH152, surface expression; pJH153, intracellular expression; pJH154, secreted expression. HIV-1 envelopes also constructed in hygromycin resistant mycobacterial expression vectors such as pYUB2051, pYUB2052, and pYUB2053.

TABLE 3

Summary of r-*m. smegmatis* immunization data. Ability of Recombinant *M. smegmatis* Expressing Group M Consensus Envelope gp120 and gp140CF to Prime for a Recombinant Group M Consensus Env gp140CF Protein Boost

| Prime X2 | Boost X1 | Anti HIV-1 gp140 Geometric Mean Titer (n = 5 mice) |
|---|---|---|
| *M. smeg* empty plasmid control | rgp140CF 50 ug protein | 609 |
| *M. smeg*-pJH154 gp120 secreted | rgp140CF 50 ug protein | 7,211* |
| *M. smeg*-pJH154 gp140CF secreted | rgp140CF 50 ug protein | 4,497* |
| None | rgp140CF 50 ug protein | 758 |

Dose of *M. smegmatis* = $10^8$ or $10^9$ CFU.
*= p < .05 compared control

Table 3. Summary of r*M. smegmatis* immunization data. Table 3 shows a summary of end-point titers of mouse study groups. End-point titers are determined when OD E/C is equal to or greater than 3. Our results show that the immunization via intraperitoneal (IP) is better antibody reactivity than intradermal (ID) injection. Mice groups immunized by CON6-gp120 gave better antibody reactivity than those immunized by CON6-gp140CF. It also indicated that the expression of HIV ENV as a secreted antigen would be better (pJH154-gp120/*M. smegmatis*). Interestingly, there was no dose effect and the highest dose ($10^{10}$ CFU) showed very low immune response. There were two controls in this study: one was the immunization of *M. smegmatis* harboring no mycobacterial plasmid/constructs and the other was of *M. smegmatis* harboring empty pJH222 plasmid. Comparing and statistical analysis between individual groups among intraperitoneal immunization is showed in the right column. For example, the comparison of group G2/G13 (*M. smegmatis* vs pJH153-gp120/*M. smegmatis* as $10^9$ CFU) is showed in the table as statistically significant (p<0.01). Another example was the comparison of G7/G18 (Empty pJH222/*M. smegmatis* vs pJH154-gp120/*M. smegmatis* as $10^7$ CFU), which was statistically significant (0.01<p<0.02). This data were used to establish that the mouse immunization study of BCG strains will use intraperitoneal injection and immunization with moderate dosage. It showed pJH154, which designed to deliver target protein as a secreted antigen, is a better choice to express HIV envelopes in BCG.

Example 3

Further Optimization of Expression of *P. falciparium* MSP Antigen

The XbaI/BamHI fragment, which contains the α-antigen promoter, 19 kD signal sequence and msp1.19 (Example 1) was amplified from pJH222 and cloned in pMV261 replacing the XbaI/BamHI fragment. Fragment 1 or Fragment 2 of msp1.42 (FIG. 16) were cloned in the vector replacing msp1.19. The final construct was transformed into *Mycobacterium smegmatis*, $mc^2155$ and protein lysate from 1 ml of culture was extracted and analyzed by SDS-PAGE and Western. Protein bands specific to monoclonal antibody *Plasmodium falciparum*, mAb 5.2 (MRA-94, Malaria Research and Reference Reagent Resource Center) were visualized after incubation with a secondary antibody, (NA 931V, Amersham Biosciences; anti-mouse IgG linked to horse radish peroxidase). As shown in FIG. 16, Fragment 1, containing most of the MSP 1.33 clone, exhibited much greater expression of the MSP antigen.

Example 4

Further Characterization of *M. smegmatis* Expressing the HIV-1 gp120 Antigen r*M. smegmatis* elicited HIV-1 Env-specific CD4+ T cells in mice. To determine the ability of *M. smegmatis* vector and other vaccine vectors to elicit gp120-specific $CD4^+$-T-cell responses, splenocytes from immunized mice were exposed in vitro to a pool of peptides spanning the HIV-1 gp120 protein. As shown in FIG. 17, immunization of mice with Smeg-gp120 elicited HIV-1-specific $CD4^+$ T cells that produced levels of IFN-γ comparable to those produced by $CD4^+$ T cells from Vaccinia-gp160 or DNA-gp120 immunized mice, and higher than those produced by $CD4^+$ T cells from mice immunized with Ad-gp140. IL-2 production by gp120-specific $CD4^+$ T cells was comparable in Smeg-gp120 and Vac-gp160 immunized mice and increased following boosting. Interestingly, production of IL-2 by gp120-specific $CD4^+$ T cells of DNA-gp120 immunized mice was the highest at the time of the peak immune responses following the prime and boost immunization, but did not appear to be durable, since it decreased by week 10 following the priming immunization. As in the case of IFN-□ production, gp120-specific $CD4^+$ T cells of mice immunized with Ad-gp140 produced the lowest IL-2 levels. These findings indicate that Smeg-gp120 immunized mice develop Th1-type immune responses that rapidly gain memory function.

r*M. smegmatis* vector efficiently primed T cell responses in a prime/boost immunization strategy. Although the frequency of p18-specific splenic $CD8^+$ T cells in the r*M. smegmatis* immunized mice was not as high as that seen in mice that received the other immunogens, the phenotypic evidence that these cells were predominantly memory T lymphocytes encouraged us to evaluate *M. smegmatis* as a priming vector in a heterologous immunization regimen. Since plasmid DNA is currently used as the primary vaccine modality in many prime/boost vaccine regimens in advanced clinical trials, we chose to compare r*M. smegmatis* with plasmid DNA in this study. Groups of mice were injected a single time with Smeg-gp120 or DNA-gp120 and 20 weeks later the mice were boosted with a suboptimal dose ($10^6$ particles) of Ad-gp140. Other groups of mice were injected twice with Smeg-gp120 or DNA-gp120, 10 weeks apart, and 10 weeks later boosted with Ad-gp140. FIG. 18A shows the phenotypic profile of the p18-specific CD8$^+$ T cells in the peripheral blood of each group of immunized mice on the day of the Ad-gp140 boost. In mice primed with Smeg-gp120, more than 93% of the p18-specific CD8$^+$ T cells expressed CD62L and CD27, surface molecule associated with T cell memory function, while in DNA-gp120 primed mice only 50% of the p18-specific CD8$^+$ T-cell expressed CD62L and 70% expressed CD27. The differences between the phenotypic profiles of the p18-specific CD8$^+$-T-cell elicited by these two vectors were more marked after two immunizations. In the Smeg-gp120 immunized mice 85% and 92% of these epitope-specific cells expressed CD62L and CD27, respectively, while in the DNA-immunized mice only 15% and 35% of p18-specific CD8$^+$ T cells expressed CD62L and CD27, respectively. No significant differences were observed in the expression of CD127 by p18-specific CD8$^+$ T-cells in the Smeg-gp120 and DNA-gp120 immunized mice. The Smeg-gp120 and DNA-gp120 immunized mice also differed in the level of p18-specific CD8$^+$ T cells seen in their peripheral blood. On the day of Ad-gp140 boosting, the Smeg-gp120 and DNA-gp120 immunized mice demonstrated 0.05% and 0.5% p18-specific CD8$^+$ T cells, respectively, and the second immunization increased these percentages to 0.2% and 4.0%, respectively. Thus, although the Smeg-gp120 immunized mice had gp120-specific CD8$^+$ T lymphocytes that were predominantly memory cells, the tetramer-positive cells were a much smaller percent of the CD8$^+$ T cell population in these mice.

The mice were then inoculated with a suboptimal dose of Ad-gp140 ($10^6$ particles) and the kinetics of the generation of p18-specific CD8$^+$ T cells were assessed. The use of a suboptimal dose of Ad-gp120 was chosen to facilitate discrimination between the priming efficiency of plasmid DNA and rM. smegmatis immunogens. One week after the Ad-gp140 immunization, the DNA-immunized mice (one or two immunizations) had generated higher p18-specific CD8$^+$ T cell responses than the Smeg-gp120 immunized mice (FIG. 8B). However, by the second and third weeks post-immunization, Smeg-gp120 immunized mice had comparable p18-specific CD8$^+$ T cell responses. The contraction phase of Smeg-gp120 and DNA-gp120 immunized mice was similar as well and the magnitude of the p18-specific CD8+ T cells was equal for long time. Therefore, in spite having a low percentage of p18-specific CD8$^+$ T cells, the Smeg-gp120 immunized mice developed robust secondary CD8$^+$ T cell responses specific for this viral epitope.

Figure 19:
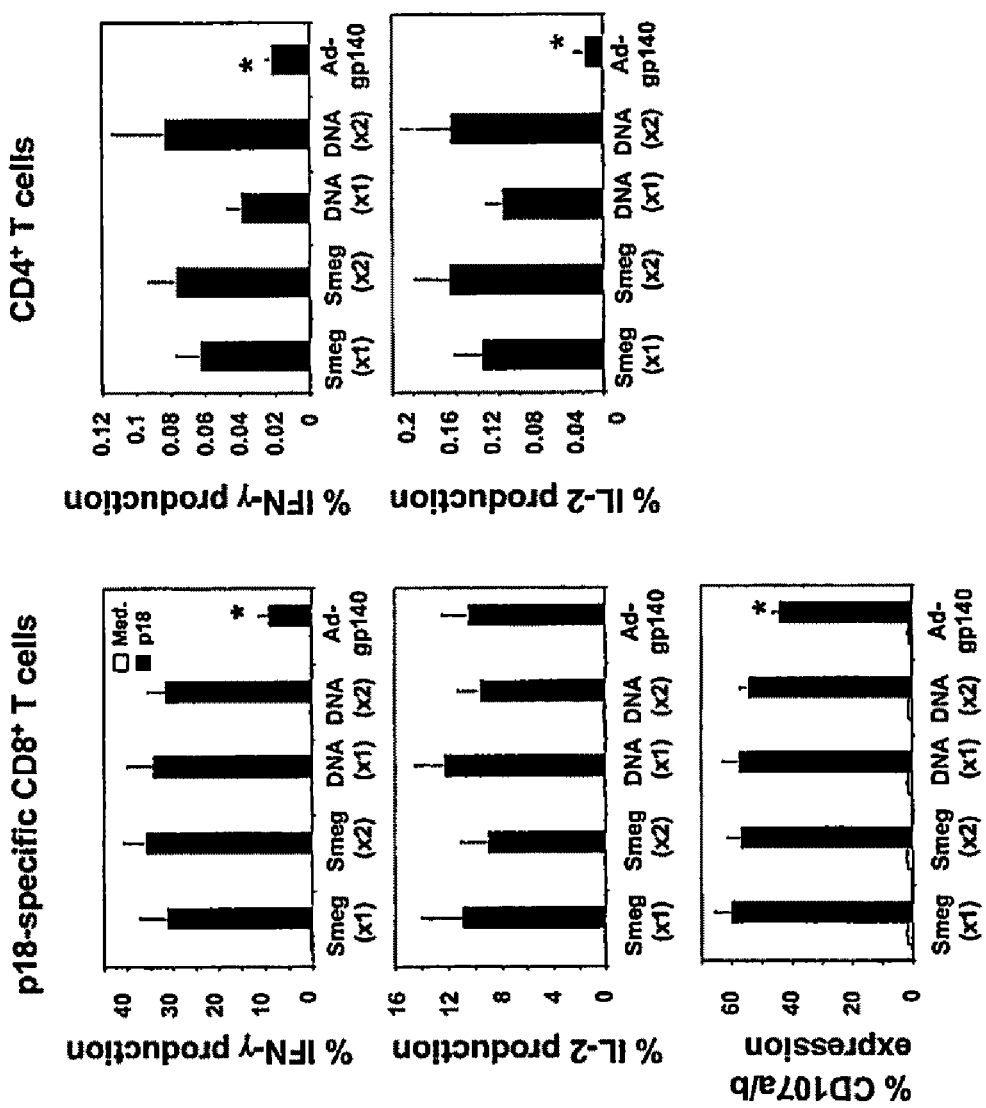
FIG. 19 is graphs showing a functional analysis of the p18-specific CD8+ T cells and CD4+ T cells elicited by priming with Smeg-gp120 or DNA-gp120 followed by boosting with Ad-gp140. Mice were immunized either once (×1) or twice (×2), 10 weeks interval, with Smeg-gp120 ($5 \times 10^7$ CFU) or DNA-gp120 (50 μg). 20 weeks after the first immunization and 10 weeks after the second immunization the mice were inoculated with $10^6$ particles of Ad-gp140. Splenocytes were harvested 8 weeks after the immunization with Ad-gp140 and were cultured for 6 hr in the presence of medium alone, p18 peptide (2 μg/ml) or Env peptide pool (1 μg/ml). Intracellular production of IFN-γ and IL-2 by CD8+ p18-specific T cells and CD4+ T cells or CD107a/b expression by p18-specific CD8+ T cells were evaluated. Data are presented as the percentages of tetramer positive CD8+ T cells staining positively for IFN-γ, IL-2 or CD107a/b, and CD4+ T cells staining positively for IFN-γ or IL-2 and represent the means of five mice per group ±SE.
Figure 20:
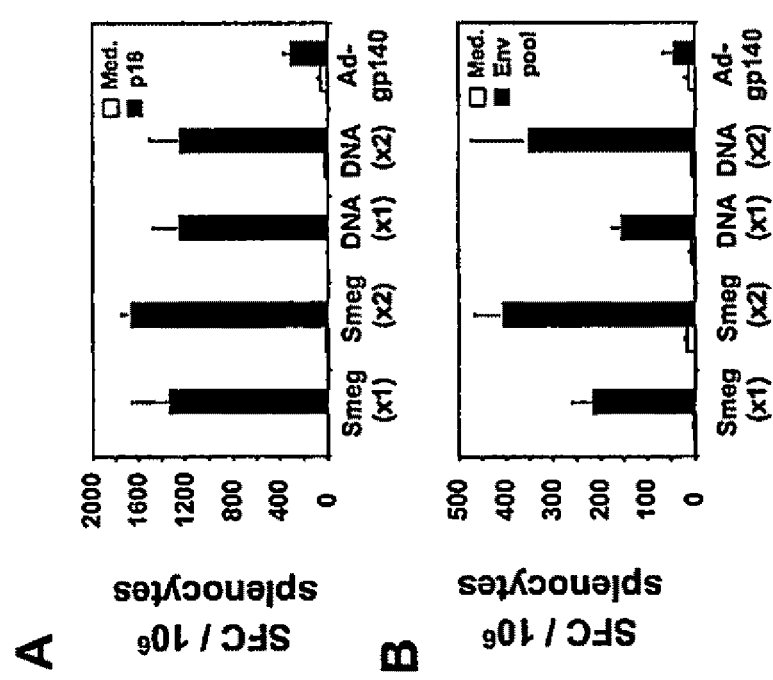
FIG. 20 is graphs showing IFN-γ production by CD4+ and CD8+ T cells following priming immunization with Smeg-gp120 or DNA-gp120, and boosting immunization with Ad-gp140. Mice were immunized either once (×1) or twice (×2), 10 weeks apart, with Smeg-gp120 (5×10$^7$ CFU) or DNA-gp120 (50 µg). Twenty weeks after the first immunization and 10 weeks after the second immunization the mice were inoculated with 10$^6$ particles of Ad-gp140. Splenocytes were harvested from individual mice 8 weeks after the immunization with Ad-gp140. IFN-γ productions were evaluated by ELISPOT assay using total splenocytes incubated with p18 peptide (1 µg/ml) (Panel A) or by CD8$^+$ depleted splenocytes stimulated with peptide pool consisted of 158 overlapping 15-mer peptides spanning the HIV-1 HXB2/BaL Env protein at a concentration of 1 µg/ml (Panel B). Data are presented as the mean number of antigen-specific spot per 10$^6$ spleen cells ±SE with five mice per group.

Heterologous recombinant M. smegmatis prime/recombinant Adenovirus vector boost immunization elicited IL-2 and IFN-γ secreting HIV-1 specific CD4+ and CD8+ T cells. The functional properties of the antigen-specific CD4+ and CD8+ T cell responses generated in mice that received a recombinant M. smegmatis prime followed by a recombinant adenovirus boost was next evaluated. Priming of mice with either Smeg-gp120 or DNA-gp120 followed by Ad-gp140 boosting elicited higher frequency of HIV-1 p18-specific CD8$^+$ T cells that secreted IFN-γ and were cytotoxic (measured by expression of CD107a and CD107b) compared to immunization with Ad-gp140 alone (FIGS. 19 and 20). The heterologous prime/boost immunization also generated HIV-1 specific CD4$^+$ T cells that secreted IFN-γ and IL-2. Furthermore, more IFN-γ-producing CD4$^+$ T cells were elicited in mice after two immunizations with Smeg-gp120 or DNA-gp120 than with a single immunization with either vector (FIG. 20B). Altogether, these data suggest that recombinant M. smegmatis can prime functional antigen-specific CD4+ and CD8+ T cell responses as efficiently as plasmid DNA.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A vaccine comprising a recombinant mycobacterium expressing an HIV-1 antigen and a malarial antigen, wherein the mycobacterium is *Mycobacterium smegmatis*, the *Mycobacterium smegmatis* expresses full length HIV-1 gp120 envelope protein, said vaccine elicits both effector and memory HIV-1 envelope-specific CD8+ T cells, and HIV-1 envelope-specific CD4+ T cells, and said malarial antigen is pfMSP1.19 or pfMSP1.42.

2. The vaccine of claim 1, wherein the malarial antigen is PfMSP1.42.

3. The vaccine of claim 1, wherein the malarial antigen is PfMSP1-19.

4. The vaccine of claim 1, wherein the HIV-1 antigen and malarial antigen are expressed from genes under the control of a mycobacterial promoter, wherein the mycobacterial promoter for the HIV-1 antigen and the malarial antigen are independently hsp60, mtrA, 18kD, α-Ag, or aceA.

5. The vaccine of claim 4, wherein the mycobacterial promoter for the HIV-1 antigen and the malarial antigen is α-Ag.

6. The vaccine of claim 1, wherein the HIV-1 antigen and the malarial antigen are each expressed from a gene further encoding a signal sequence that facilitates expression of each antigen in the mycobacterial membrane.

7. The vaccine of claim 6, wherein the signal sequence is a 19-kDa signal sequence.

8. The vaccine of claim 1, wherein
the HIV-1 antigen and the malarial antigen are each expressed from a gene further encoding a 19-kDa signal sequence; and
the mycobacterial promoter for the HIV-1 antigen and the malarial antigen is α-Ag.

9. A method of inducing an immune response in a mammal against HIV-1 and a malarial pathogen, the method comprising infecting the mammal with the vaccine of claim 1.

10. A vaccine comprising *Mycobacterium smegmatis* expressing full length HIV-1 gp120 envelope protein, wherein said vaccine elicits both effector and memory HIV-1 envelope-specific CD8+ T cells, and HIV-1 envelope-specific CD4+ T cells.

11. The vaccine of claim 10, wherein the HIV-1 antigen is expressed from a gene further encoding a 19-kDa signal sequence.

12. The vaccine of claim 10, wherein a mycobacterial promoter for the HIV-1 antigen is α-Ag.

13. The vaccine of claim 10, wherein
the HIV-1 antigen is expressed from a gene further encoding a 19-kDa signal sequence; and
the mycobacterial promoter for the HIV-1 antigen is α-Ag.

14. A method of inducing an immune response in a mammal against HIV-1, the method comprising infecting the mammal with the vaccine of claim 10.

* * * * *